United States Patent
Palan et al.

(10) Patent No.: US 10,307,468 B2
(45) Date of Patent: Jun. 4, 2019

(54) **MANUFACTURE OF DI-CHAIN RECOMBINANT *CLOSTRIDIUM BOTULINUM* NEUROTOXINS USING LYS-C AND A HYDROPHOBIC SURFACE**

(71) Applicant: IPSEN BIOINNOVATION LIMITED, Abingdon, Oxfordshire (GB)

(72) Inventors: Shilpa Palan, Abingdon (GB); Sai Man Liu, Abingdon (GB); Gavin Stephen Hackett, Abingdon (GB)

(73) Assignee: IPSEN BIOINNOVATION LIMITED, Abingdon, Oxfordshire ( * ) Notice: Subject to any disclaimer, the term of this patent is extended or adjusted under 35 U.S.C. 154(b) by 0 days.

(21) Appl. No.: 15/306,006

(22) PCT Filed: Apr. 29, 2015

(86) PCT No.: PCT/GB2015/051250
§ 371 (c)(1),
(2) Date: Oct. 21, 2016

(87) PCT Pub. No.: WO2015/166242
PCT Pub. Date: Nov. 5, 2015

(65) Prior Publication Data
US 2018/0117128 A1 May 3, 2018

(30) Foreign Application Priority Data
Apr. 29, 2014 (GB) .................................. 1407525.3

(51) Int. Cl.
| | | |
|---|---|---|
| *C12P 21/06* | (2006.01) | |
| *A61K 38/48* | (2006.01) | |
| *A61K 47/02* | (2006.01) | |
| *A61K 47/26* | (2006.01) | |
| *C12N 9/64* | (2006.01) | |

(52) U.S. Cl.
CPC .......... *A61K 38/4893* (2013.01); *A61K 47/02* (2013.01); *A61K 47/26* (2013.01); *C12N 9/6489* (2013.01); *C12P 21/06* (2013.01); *C12Y 304/24069* (2013.01); *Y02A 50/469* (2018.01)

(58) Field of Classification Search
CPC ................................................. A61K 38/4893
See application file for complete search history.

(56) References Cited

U.S. PATENT DOCUMENTS

2006/0228780 A1* 10/2006 Luo .................. C07K 14/33
435/69.1

FOREIGN PATENT DOCUMENTS

| EP | 2 524 963 | * 11/2012 | ............... C12N 9/54 |
|---|---|---|---|
| EP | 2 524 963 A1 | 11/2012 | |
| WO | 0033863 A2 | 6/2000 | |
| WO | 2014080206 A1 | 5/2014 | |

OTHER PUBLICATIONS

Yao Zhao et al., "Peg Precipitation Coupled with Chromatography is a New and Sufficient Method for the Purification of Botulinum Neurotoxin Type B", PLOS ONE, vol. 7, No. 6, Jun. 28, 2012, pp. e39670.
Andy Pickett et al., "Towards New uses of Botulinum Toxin as a Novel Therapeutic Tool", Toxins, vol. 3, No. 12, Jan. 12, 2011, pp. 63-81.
C. Malizio et al., "Purification of Clostridium botulinum Type A Neurotoxin", Methods in Molecular Biology, Humana Press, Inc., U.S., vol. 145, Jan. 1, 2000, pp. 27-39.
Clifford C. Shone e al., "Inactivation of Clostridium botulinum type A neurotoxin by trypsin and purification of two tryptic fragments. Proteolytic action near the COOH-terminus of the heavy subunit destroys toxin-binding activity", European Journal Biochemistry, vol. 151, No. 1, Aug. 1, 1985, pp. 75-82.
V. Sathyamoorthy et al., "Separation, Purification, Partial Characterization and Comparison of the Heavy and Light chains of Botulinum Neurotoxin Types A, B, and E", The Journal of Biological Chemistry, vol. 260, No. 19, Sep. 5, 1985, pp. 10461-10466.
L. Bruce Pearce et al., "Measurement of Botulinum Toxin Activity: Evaluation of the Lethality Assay", Toxicology and Applied Pharmacology, vol. 128, 1994, pp. 69-77.
B. R. DasGupta et al., "Purification and Amino Acid Composition of Type A Botulinum Neurotoxin", Toxicon, vol. 22, No. 3, 1984, pp. 415-424.
W. H. Jost et al., "Botulinum Neurotoxin Type A Free of Complexing Proteins (XEOMIN) in Focal Dystonia", Drugs, vol. 67, No. 5, 2007, pp. 669-683.

* cited by examiner

*Primary Examiner* — Sheridan Swope
(74) *Attorney, Agent, or Firm* — Gene J. Yao; Barnes & Thornburg LLP

(57) ABSTRACT

Methods for producing di-chain BoNT/A from single chain BoNT/A using Lys-C followed by purification using a hydrophobic surface.

10 Claims, 15 Drawing Sheets

Figure 1:
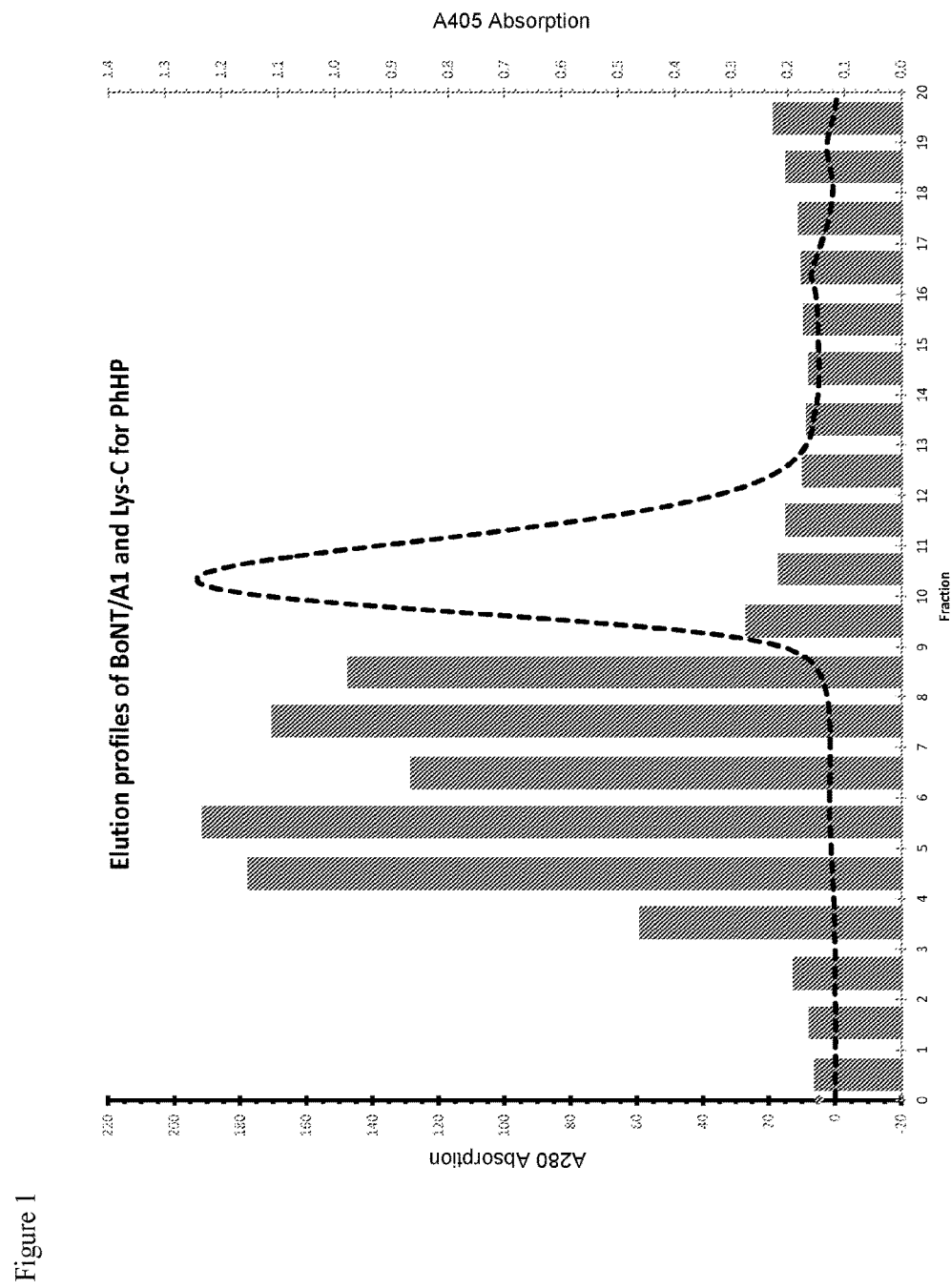

Specification includes a Sequence Listing.

MANUFACTURE OF DI-CHAIN RECOMBINANT *CLOSTRIDIUM BOTULINUM* NEUROTOXINS USING LYS-C AND A HYDROPHOBIC SURFACE

CROSS REFERENCE TO RELATED APPLICATIONS

This application is a U.S. national stage filing of International Patent Application No. PCT/GB2015/051250, filed Apr. 29, 2015, which claims the priority of United Kingdom Application No. 1407525.3, filed Apr. 29, 2014.

REFERENCE TO SEQUENCE LISTING

The instant application contains a Sequence Listing that has been submitted electronically in ASCII format and is hereby incorporated by reference in its entirety. Said ASCII copy, created on Mar. 25, 2019, is named 15306006SeqListing.txt and is 37,177 bytes in size.

FIELD OF THE INVENTION

The present invention relates to methods for producing recombinant *Clostridium botulinum* (*C. botulinum*) neurotoxins of serotype A (BoNT/A).

BACKGROUND OF THE INVENTION

Botulinum neurotoxin (BoNT) is produced by *C. botulinum* in the form of a large protein complex, consisting of BoNT itself complexed to a number of accessory proteins. There are at present at least seven different classes of botulinum neurotoxin, namely: botulinum neurotoxin serotypes A, B, $C_1$, D, E, F and G, all of which share similar structures and modes of action. A possible eighth serotype, H, has recently been reported but the sequence is not yet published. Different BoNT serotypes can be distinguished based on inactivation by specific neutralising anti-sera, with such classification by serotype correlating with percentage sequence identity at the amino acid level. BoNT proteins of a given serotype are further divided into different subtypes on the basis of amino acid percentage sequence identity.

BoNTs are the most potent toxins known, with median lethal dose (LD50) values for mice ranging from 0.5 to 5 ng/kg depending on the serotype. BoNTs are adsorbed in the gastrointestinal tract, and, after entering the general circulation, bind to the presynaptic membrane of cholinergic nerve terminals and prevent the release of the neurotransmitter acetylcholine. BoNT/B, BoNT/D, BoNT/F and BoNT/G cleave synaptobrevin/vesicle-associated membrane protein (VAMP); BoNT/C, BoNT/A and BoNT/E cleave the synaptosomal-associated protein of 25 kDa (SNAP-25); and BoNT/C cleaves syntaxin.

In nature, clostridial neurotoxins are synthesised as a single-chain polypeptide that is modified post-translationally by a proteolytic cleavage event to form two polypeptide chains joined together by a disulphide bond. Cleavage occurs at a specific cleavage site, often referred to as the activation site, that is located between the cysteine residues that provide the inter-chain disulphide bond. It is this di-chain form that is the active form of the toxin. The two chains are termed the heavy chain (H-chain), which has a molecular mass of approximately 100 kDa, and the light chain (L-chain or LC), which has a molecular mass of approximately 50 kDa. The H-chain comprises a C-terminal targeting component ($H_C$ domain) and an N-terminal translocation component ($H_N$ domain). The cleavage site is located between the L-chain and the translocation components, in an exposed loop region (see Table 1). Following binding of the $H_C$ domain to its target neuron and internalisation of the bound toxin into the cell via an endosome, the $H_N$ domain translocates the L-chain across the endosomal membrane and into the cytosol, and the L-chain provides a protease function (also known as a non-cytotoxic protease).

Non-cytotoxic proteases act by proteolytically-cleaving intracellular transport proteins known as SNARE proteins (e.g. SNAP-25, VAMP, or Syntaxin)—see Gerald K (2002) "Cell and Molecular Biology" (4th edition) John Wiley & Sons, Inc. The acronym SNARE derives from the term Soluble NSF Attachment Receptor, where NSF means N-ethylmaleimide-Sensitive Factor. SNARE proteins are integral to intracellular vesicle fusion, and thus to secretion of molecules via vesicle transport from a cell. The protease function is a zinc-dependent endopeptidase activity and exhibits a high substrate specificity for SNARE proteins. Accordingly, once delivered to a desired target cell, the non-cytotoxic protease is capable of inhibiting cellular secretion from the target cell. The L-chain proteases of Clostridial neurotoxins are non-cytotoxic proteases that cleave SNARE proteins.

Botulinum neurotoxins are well known for their ability to cause a flaccid muscle paralysis. Said muscle-relaxant properties have led to botulinum neurotoxins (such as BoNT/A) being employed in a variety of medical and cosmetic procedures, including treatment of glabellar lines or hyperkinetic facial lines, headache, hemifacial spasm, hyperactivity of the bladder, hyperhidrosis, nasal labial lines, cervical dystonia, blepharospasm, and spasticity.

Traditionally, production of BoNT was carried out by culture of *C. botulinum* bacteria, followed by isolation and purification of the botulinum neurotoxin complex. However, production of BoNT in this way is inefficient and provides low protein yields. In addition, *C. botulinum* are spore-forming bacteria and therefore require specialist culture equipment and facilities, which are not required for the culture of bacteria such as *Escherichia coli* (*E. coli*). The increasing use of BoNTs led to the development of alternative methods for producing and purifying BoNT. In particular, methods of producing BoNTs using *E. coli* have been developed.

The purification of the CNTs from the fermentation solution (whether using *C. botulinum* or *E. coli*) is a particular challenge, since the neurotoxins are contained therein as a mixture of unprocessed, partially processed and fully processed polypeptides, all of which have very similar biochemical and physical properties. Partially processed neurotoxins are typically generated, if the endoproteolytic activity has hydrolysed the peptide bond between the light chain and the loop, while the peptide bond between the loop and the N-terminus of the heavy chain is still intact. Moreover, partially processed neurotoxin can also be created if the endoproteolytic activity has released the loop peptide from the heavy chain, while the peptide bond between the loop peptide and the C-terminus of the light chain has not yet been hydrolysed. Depending on the conditions of fermentation and the type of neurotoxin, the fully processed polypeptide which is devoid of the loop peptide can be contaminated significantly, with between 5% to 90% partially processed or unprocessed polypeptide. In some cases, the neurotoxin is mainly unprocessed and, prior to therapeutic use, needs to be treated with an endopeptidase in order to become biologically active.

The prior art describes various attempts to treat clostridial neurotoxins with heterologous proteases in order to reduce the amount of unprocessed or partially processed precursor protein. The protease most widely used for activation of clostridial neurotoxins, Trypsin, while being useful for activating clostridial neurotoxins of serotypes B (BoNT/B) and E (BoNT/E) appears to produce secondary products, presumably by proteolytic action near the C-terminus of the heavy subunit of BoNT/A and, thus, appears to destroy toxin binding to its cellular receptor. More specific cleavage products are theoretically expected from endogenous proteases, isolated from the native host, such as C. botulinum producing BoNT/A.

The present inventors have previously identified various proteases, such as endogenous proteases from C. botulinum and exogenous proteases including the protease endoproteinase Lys-C(Lys-C) (which is commercially available and may be isolated from Lysobacter enzymogenes). However, although cleavage of recombinant BoNT/A by this endoproteinase more accurately mirrors native cleavage, the use of Lys-C raises new practical considerations. In particular, after cleavage of recombinant BoNT/A, Lys-C can remain active in the reaction mixture for days. Therefore, means and methods for reducing the amount of Lys-C in the final product and thereby improving the quality of neurotoxin preparations are highly desirable but not yet available.

Thus, a technical problem underlying the present invention may be seen as the provision of means and methods for improving the manufacture of neurotoxin polypeptides by complying with the aforementioned needs. Specifically, there is a need in the art for improved methods for producing recombinant BoNTs, in particular activated di-chain recombinant BoNT/A.

The technical problem is solved by the embodiments characterised in the claims and herein below.

SUMMARY OF THE INVENTION

The production of recombinant BoNT/A sub-serotypes can be achieved by expression in *Escherichia coli* as a single polypeptide, herein referred to as single-chain BoNT/A proteins. Upon isolation of this single-chain protein by fast protein liquid chromatography (FPLC), the single-chain protein must be cleaved to form the active toxin, which is a di-chain protein linked together by a single disulfide bond.

The present inventors have previously found that recombinant single-chain BoNT/A sub-serotypes can be cleaved using the protease endoproteinase Lys-C(Lys-C) to produce the active di-chain BoNT/A protein neurotoxin, i.e. a heterodimer of the BoNT/A light and heavy chains. The Lys-C cleavage site was determined to be identical to the endogenous protein by N-terminal sequencing and mass spectrometry. Thus, production of the active di-chain BoNT/A protein using Lys-C is advantageous, because it results in production of an authentic active di-chain BoNT/A, namely a di-chain BoNT/A that is essentially identical to the native active di-chain BoNT/A. In contrast, trypsin, another common protease used to produce active di-chain BoNT proteins, cleaves at least one additional site within the BoNT/A single-chain sequence.

This additional cleavage reduces the potency of the active di-chain BoNT/A protein produced.

Once the single-chain BoNT/A protein has been cleaved by Lys-C, the active di-chain BoNT/A protein requires purification to remove any remaining host cell proteins and the Lys-C protease in order to produce the final pure product.

In particular, from endoproteinase Lys-C cleavage tests, the inventors have found that Lys-C cleaves recombinant BoNT/A1 (rBoNT/A1) at very low concentrations and remained active over a period of days. Consequently, it is important to develop a method that could purify this protease away from the activated toxin.

The present inventors have developed an efficient method to remove the activating Lys-C protease and host cell proteins from the BoNT/A after activation by using hydrophobic interaction chromatography (HIC). The present inventors surprisingly found that HIC maximises not only the amount of active di-chain BoNT/A recovered in the purification, but also significantly improves the Lys-C resolution, i.e. removal of the Lys-C protease. The advantageous properties of HIC are counterintuitive when considering that the biophysical characteristics of Lys-C and rBoNT/A; based on the isoelectric point (pI) and net charge of the BoNT/A and Lys-C, it is predicted that ion exchange chromatography (IEX) would resolve the two proteins rather than HIC.

The present invention solves one or more of the above-mentioned problems, by providing methods as specified in the claims.

Accordingly, the present invention provides a method for producing soluble di-chain BoNT/A protein, said method comprising:
  a) providing a soluble single-chain BoNT/A protein;
  b) contacting said BoNT/A protein with endoproteinase Lys-C(Lys-C) in solution; and
  c) separating the soluble BoNT/A protein from the Lys-C by contacting the solution containing soluble BoNT/A protein and Lys-C with a hydrophobic surface, wherein the soluble BoNT/A protein preferentially binds to the hydrophobic surface.

The soluble single-chain BoNT/A protein may be produced in a host cell, by expressing a nucleic acid encoding said single-chain BoNT/A protein in a expression system, wherein optionally the expression system is a bacterial expression system, preferably wherein the bacterial expression system is an *E. coli* expression system and the host cell is an *E. coli* cell. Said soluble single-chain BoNT/A protein may be expressed in the cytoplasm of said host cell, or in a cell-free system. The soluble single-chain BoNT/A protein may be expressed at a level of at least 5 mg/L of culture. Said method may comprise lysis of the host cell to provide a host cell homogenate containing said soluble single-chain BoNT/A protein (preferably the soluble single-chain BoNT/A is present at a concentration of at least 5 mg/L of the host cell homogenate).

The hydrophobic surface used in the method of the present invention may be an inert matrix to which a ligand consisting of aryl or alkyl groups is attached, wherein optionally the ligand is selected from the group consisting of: butyl, phenyl or octyl ligands. In one embodiment a high performance hydrophobic surface is used.

The invention also provides an active di-chain BoNT/A protein obtainable by the method of the invention.

The invention further provides a composition comprising an active di-chain BoNT/A protein of the invention; wherein said composition is substantially free from endoproteinase Lys-C. Preferably said composition contains less than 400 pg endoproteinase Lys-C(Lys-C) per 100 ng BoNT/A protein, or less than 300 pg Lys-C per 100 ng BoNT/A protein, or less than 200 pg Lys-C per 100 ng BoNT/A protein, or less than 100 pg Lys-C per 100 ng BoNT/A protein, or less than 50 pg Lys-C per 100 ng BoNT/A protein. Such compositions are suitable for use in therapeutic and cosmetic treatments.

The invention also provides a liquid pharmaceutical composition comprising: an active di-chain BoNT/A protein of the invention; a non-protein stabilising agent that is a surfactant; and water; wherein said liquid pharmaceutical composition does not comprise a protein stabilising agent; and wherein said liquid pharmaceutical composition is substantially free from endoproteinase Lys-C(Lys-C). Preferably said liquid pharmaceutical composition contains less than 400 pg Lys-C per 100 ng BoNT/A protein, or less than 300 pg Lys-C per 100 ng BoNT/A protein, or less than 200 pg Lys-C per 100 ng BoNT/A protein, or less than 100 pg Lys-C per 100 ng BoNT/A protein, or less than 50 pg Lys-C per 100 ng BoNT/A protein. Said liquid pharmaceutical composition may further comprise: sodium chloride, a buffer to maintain pH between 5.5 and 7.5, and a disaccharide; wherein the water is sterile water.

The invention also provides an active di-chain BoNT/A protein, composition, or liquid pharmaceutical composition of the invention for use in therapy.

The invention further provides the use of an active di-chain BoNT/A protein, composition, or liquid pharmaceutical composition of the invention in the manufacture of a medicament.

The invention also provides a method of treatment comprising administration of an active di-chain BoNT/A protein, composition, or liquid pharmaceutical composition of the invention to a patient in need thereof.

DETAILED DESCRIPTION OF THE INVENTION

Botulinum Toxin Serotype A (BoNT/A)

The term "BoNT" means botulinum neurotoxin and refers to neurotoxin obtainable from C. botulinum such as BoNT of serotype A, B, Cl, D, E, F or G. Also encompassed by the term "CNT" and "BoNT" is recombinant and modified neurotoxin comprising one or more modifications including chemical modification or genetic modification. The term "genetic modification" means deletion, substitution or addition of one or more nucleic acid residues resulting in the deletion, substitution or addition of one or more amino acid bases, or the deletion, substitution or addition of said one or more amino acid residues.

The BoNT/A serotype is divided into at least eight sub-serotypes (also known as subtypes), BoNT/A1 to BoNT/A8, which share at least 84%, up to 98%, amino acid sequence identity; BoNT/A proteins within a given subtype share a higher amino acid percentage sequence identity. Table 1 (below) shows the precursor, the native di-chain neurotoxin of BoNT/A subtypes and identifies the exposed loop (activation loop) comprising the amino acid sequence cleaved by Lys-C.

TABLE 1

| Toxin | exposed (activation) loop | LC | $H_N$ | $H_{CN}$ | $H_{CC}$ |
|---|---|---|---|---|---|
| BoNT/A1 (P10845) | SEQ ID NO: 2 | M1-K438 | A449-N872 | I873-S1092 | N1093-L1296 |
| BoNT/A2 (A2I2R5) | SEQ ID NO: 3 | M1-K438 | A449-N872 | I873-S1092 | N1093-L1296 |
| BoNT/A2 (A2I2R5) | SEQ ID NO: 4 | M1-K434 | A445-N868 | I869-S1088 | N1089-L1292 |
| BoNT/A3 (B1L2G5) | SEQ ID NO: 3 | M1-K438 | A449-N872 | I873-S1092 | N1093-L1296 |
| BoNT/A3 (B1L2G5) | SEQ ID NO: 4 | M1-K434 | A445-N868 | I869-S1088 | N1089-L1292 |
| BoNT/A3 (Q3LRX9) | SEQ ID NO: 5 | M1-K434 | A445-N868 | I869-S1088 | N1089-L1292 |
| BoNT/A4 (Q3LRX8) | SEQ ID NO: 6 | M1-K438 | A449-N872 | I873-S1092 | N1093-L1296 |
| BoNT/A5 (C7BEA8) | SEQ ID NO: 7 | M1-K438 | A449-N872 | I873-S1092 | N1093-L1296 |
| BoNT/A6 (C9WWY7) | SEQ ID NO: 2 | M1-K438 | A449-N872 | I873-S1093 | N1094-L1297 |
| BoNT/A7 (K4LN57) | SEQ ID NO: 13 | M1-K438 | A449-N872 | I873-S1092 | N1093-L1296 |
| BoNT/A8 (A0A0A7PDB7) | SEQ ID NO: 14 | M1-K438 | A449-N872 | I873-S1093 | N1094-Q1297 |

Referring to Table 1, the amino acid positions (residues) indicated for the LC, $H_N$, $H_{CN}$ and $H_{CC}$ regions correspond to the amino acid positions for said regions in a full length BoNT/A protein sequence. The UniProt Accession Numbers given in Table 1 are examples of the different BoNT/A sub-serotypes. Thus, in one embodiment, the amino acid positions of the LC, $H_N$, $H_{CN}$ and $H_{CC}$ regions indicated in Table 1 correspond to the amino acid positions in the full length BoNT/A protein sequences identified by Accession Number.

Using the methods of the present invention, it is now possible to obtain BoNT/A di-chain compositions with significantly less contamination by unprocessed or partially processed BoNT/A, since those contaminants are efficiently processed into di-chain BoNT/A. The methods of the present invention also allow effective removal of the Lys-C enzyme used to process the single-chain BoNT/A protein into the active di-chain. In one aspect, the di-chain BoNT/A is a native di-chain neurotoxin, wherein the C-terminus of the light chain and the N-terminus of the heavy chain are identical to the corresponding fully processed di-chain BoNT/A isolated from wild-type clostridia.

According to the present invention, an active BoNT/A di-chain, including a recombinant BoNT/A di-chain, may be produced as a single-chain polypeptide, which is the cleaved to form the active di-chain form of the protein.

The present methods may be used to produce the di-chain of any BoNT/A subtype or a homologue or derivative thereof, including e.g. the polypeptide of SEQ ID NO: 1 and derivatives thereof. The term "derivative" as used with respect to this and other aspects of the invention, comprises amino acid mutations such as addition, substitution, deletion or truncation of one or more amino acid residues.

The BoNT/A single-chain protein may comprise a polypeptide sequence as shown in GenBank no: CBZ04958.1, YP_002805603.1, ZP_02994746.1, YP_001788403.1, YP_001782718.1, ZP_02616437.1, ZP_02614241.1, YP_001392361.1, YP_001255575.1. The BoNT/A single-chain protein may comprise a polypeptide sequence as shown in:

A1 sub-serotype: UniParc Accession No. UPI0000ED909E (UniProt Accession No. P10845, Version 159), UniParc Accession No. UPI0000EF85BD (UniProt Accession No. S8B1U4, Version 3, or UniProt Accession No. A2I2R4, version 41), UniParc Accession No. UPI0001A954C8 (UniProt Accession No. C6K838, Version 11), UniParc Accession No. UPI0000001386 (UniProt Accession No. A5HZZ9, Version 57), UniParc Accession No. UPI000003409D (UniProt Accession No. A2I2U2, Version 36), UniParc Accession No. UPI00016529B7 (UniProt Accession No. B1A2D5, Version 21), UniParc Accession No. UPI00027EE164 (UniProt Accession No. J7FGZ9, Version 6);

A2 sub-serotype: UniParc Accession No. UPI0000EF84BD (UniProt Accession No. A2I2R5, Version 28), UniParc Accession No. UPI0001C0B376 (UniProt Accession No. D2KCK3, Version 15), UniParc Accession No. UPI0001C32E84 (UniProt Accession No. D31V23, Version 10), UniParc Accession No. UPI0001F3B30D (UniProt Accession No. E5F1I1, Version 11), UniParc Accession No. UPI000016EA88 (UniProt Accession No. Q45894, Version 116 or UniProt Accession No. Q58GH1, Version 51), UniParc Accession No. UPI000067C53E (UniProt Accession No. Q2PPK6, Version 33), UniParc Accession No. UPI000290BEB1 (UniProt Accession No. K4GGE0, Version 6);

A3 sub-serotype: UniParc Accession No. UPI00005B712C (UniProt Accession No. Q3LRX9, Version 38), UniParc Accession No. UPI00016DBC11 (UniProt Accession No. B1L2G5, Version 38 or UniProt Accession No. D31V24, Version 11), UniParc Accession No. UPI000290C3D0 (UniProt Accession No. K4G3L3, Version 7);

A4 sub-serotype: UniParc Accession No. UPI00005B712D (UniProt Accession No. Q3LRX8, Version 35), UniParc Accession No. UPI00019DB885 (UniProt Accession No. C3KS13, Version 29);

A5 sub-serotype: UniParc Accession No. UPI0001AE7D6A (UniProt Accession No. C7BEA8, Version 14), UniParc Accession No. UPI000198BDAE (UniProt Accession No. E8ZMW0, Version 18 or UniProt Accession No. C1IPK2, Version 20); or A6 sub-serotype: UniParc Accession No. UPI0001B7D251 (UniProt Accession No. C9WWY7, Version 13).

A7 sub-serotype: UniParc Accession No. UPI000290B995 (UniProt Accession No. K4LN57).

A8 sub-serotype: UniParc Accession No. UPI000559A469 (UniProt Accession No. A0A0A7PDB7); UniParc Accession No. UPI0003C9D2A1 (UniProt Accession No. V5N8R1).

The BoNT/A single-chain protein may comprise a polypeptide sequence that is a homolog or derivative having at least 50% sequence identity to one of the above-mentioned BoNT/A polypeptide sequences.

In one aspect, the polypeptide chain of said BoNT/A single-chain protein comprises a sequence selected from any one of SEQ ID NOs: 2 to 7 or 13 or 14. In a more particular aspect, the polypeptide chain of said BoNT/A single-chain protein comprises a sequence selected from any one of SEQ ID NOs: 2 to 7 or 13 or 14 and wherein the second polypeptide is cleaved C-terminal to a basic amino acid residue within said sequence of any one of SEQ ID NOs: 2 to 7 or 13 or 14. Said sequences represent amino acid sequences of known substrates of the BoNT/A single-chain protein of the present invention.

BoNT/A single-chain proteins are cleaved C-terminal to a basic amino acid residue contained in the sequence, compare Table 1, column LC and $H_N$. In a preferred aspect, said BoNT/A single-chain protein comprises a sequence selected from SEQ ID NO: 2 to 7 and 13-14 (e.g. serotype BoNT/A1, SEQ ID NO: 2).

The BoNT/A single-chain protein may comprise a derivative of any one of SEQ ID NOs: 2 to 7 or 13 or 14, or of SEQ ID NO: 1, or one of the polypeptide sequences corresponding to the accession numbers identified herein, wherein said derivative has one or more point mutation and/or one or more additional amino acid residues. In another aspect, said derivative has up to 1, up to 2, up to 3, up to 4, up to 5, up to 6, up to 7, up to 8, up to 9, up to 10, up to 15 point mutations. By using the activity assay for determining protease activity, as described herein, the skilled person can determine whether a given derivative is processed by Lys-C.

The derivative may contain a point mutation changing a basic amino acid residue into a non-basic amino acid residue. The derivative may have at least 50% sequence identity with any one of SEQ ID NOs: 2 to 7 or 13 or 14, SEQ ID NO: 1, or one of the polypeptide sequences corresponding to the accession numbers identified herein. Said derivative or a polypeptide comprising the derivative may be a substrate of Lys-C and be proteolytically cleavable by Lys-C. A typical example is a derivative of SEQ ID NO: 1 comprising e.g. one or more point mutations in the light or heavy chain.

Said BoNT/A single-chain protein may comprise (a) a polypeptide sequence having at least 30% sequence identity, at least 50%, at least 60%, at least 70%, at least 80%, at least 85%, at least 90%, at least 95%, at least 96%, at least 97%, at least 98%, at least 99% or more with the sequence of SEQ ID NO: 1 (BoNT/A of ATCC 3502, Genbank acc. AAA23262), or with one of the polypeptide sequences corresponding to the accession numbers identified herein. The BoNT/A single-chain protein may comprise the polypeptide sequence of SEQ ID NO: 15, or a polypeptide sequence having at least 30% sequence identity, at least 50%, at least 60%, at least 70%, at least 80%, at least 85%, at least 90%, at least 95%, at least 96%, at least 97%, at least 98%, at least 99% or more with the sequence of SEQ ID NO: 15.

The term "sequence identity" as used herein refers to determination of the identity between a reference amino acid sequence and a query sequence wherein the sequences are aligned so that the highest order match is obtained, and which can be calculated using published techniques or methods codified in computer programs such as, for example, BLASTP, BLASTN, FASTA (Altschul 1990, J Mol Biol 215: 403). The percent identity values may be calculated over the entire amino acid sequence or over a region of the amino acid sequence. For example, for the single-chain BoNT/A protein, sequence identity may be calculated over a sequence length of up to 50 amino acid (aa) residues, up to 100aa, up to 150aa, up to 250aa, 300aa, 350aa, 400aa, 450aa, 500aa, 550aa, 600aa, 650aa, 700aa, 750aa, 800aa, 850aa, 900aa, 950aa, 1000aa, 1050aa, 1100aa, 1150aa, 1200aa, 1250aa or more residues, up to the full-length single-chain BoNT/A protein sequence. Sequence identity may be calculated over at least 50aa residues, at least 100aa, at least 150aa or at least 250aa residues.

A series of programs based on a variety of algorithms is available to the skilled worker for comparing different sequences. In this context, the algorithms of Needleman and Wunsch or Smith and Waterman give particularly reliable results. To carry out the sequence alignments and calculate the sequence identity values recited herein, the commercially available program DNASTAR Lasergene MegAlign version 7.1.0 based on the algorithm Clustal W was used over the entire sequence region with the following settings: Pairwise Alignment parameters: Gap Penalty: 10.00, Gap Length Penalty: 0.10, Protein weight matrix Gonnet 250, which, unless otherwise specified, shall always be used as standard settings for sequence alignments.

At least 30% means at least 30%, at least 40%, at least 50%, at least 85%, at least 90%, at least 95%, at least 96%, at least 97%, at least 98%, at least 99%, or more, up to 100%. The sequence identity of said BoNT/A single-chain protein sequence having at least 50% sequence identity with the sequence of SEQ ID NO: 1 may be determined based on amino acid position 420 to 466 of SEQ ID NO: 1, or said sequence identity may be determined based on any one of SEQ ID NOs: 2 to 7 or 13 or 14. In other words, a BoNT/A single-chain protein may comprise a polypeptide sequence which has e.g. at least 30% sequence identity to the polypeptide sequence found between amino acid positions 420 to 466 of BoNT/A single-chain protein or at least 30% sequence identity to the polypeptide sequence of any one of BoNT/A single-chain protein, including any one of the polypeptide sequences corresponding the the accession numbers identified herein. A polypeptide according to this definition is, e.g. obtainable from C. botulinum, C. tetani or C. sporogenes. Said BoNT/A single-chain protein may be, for example, a naturally occurring neurotoxin or a derivative thereof comprising one or more amino acid mutations such as addition, substitution, deletion or truncation of one or more amino acid residues. Encompassed are e.g. derivatives lacking e.g. the native neurotoxin $H_C$ domain or parts thereof or derivatives with other amino acid residues replacing the neurotoxin $H_C$ domain as well as derivatives with an additional light chain or another proteinaceous cargo molecule fused N-terminally to the light chain of BoNT.

The BoNT/A single-chain protein may contain additional amino acid residues at the N- or C-terminus or at an internal position. The additional amino acid residues may be flanked by one or more protease cleavage sites. The additional amino acid sequence may function as a detectable tag and/or allows binding to a solid support. An example is a His tag or a GST tag. Another example is the amino acid sequence VPPTPGSAWSHPQFEK (SEQ ID NO: 12) containing the Streptag, preferably added to the C-terminus.

In another aspect, the biological activity of said BoNT/A single-chain protein may be modulated by the proteolytic cleavage. It is well known to the skilled person, that the function of many polypeptides can be modulated by pro-teolytic processing. "Modulated" as used herein means increased or decreased, activated or inactivated. For example, the biological activity of many clostridial neurotoxins is increased or triggered by proteolytically processing a single chain neurotoxin into a di-chain neurotoxin, wherein the di-chain neurotoxin is composed of a light and a heavy polypeptide chain, which are covalently linked through a disulfide-bridge. The biological activity of the neurotoxin encompasses at least three separate activities: the first activity is a "proteolytic activity" residing in the light chain of the neurotoxin and is responsible for hydrolysing the peptide bond of one or more polypeptides involved in the regulation of cellular membrane fusion. A second activity is a "translocation activity", residing at the N-terminal end of the heavy chain of the processed neurotoxin and is involved in the transport of the light chain across the lysosomal membrane and into the cytoplasm. A third activity is a "receptor binding activity", residing at the C-terminal end of the heavy chain of the processed neurotoxin and involved in binding and uptake of the neurotoxin to a target cell. In a preferred aspect, the term biological activity as used herein means proteolytic activity. In a more preferred aspect, the term means increased proteolytic activity.

Biological activity of clostridial neurotoxin can be measured by various tests, all of which are known to the person skilled in the art. These tests allow determining one or more of the activities mentioned above. For example, the mouse $LD_{50}$ assay or the ex vivo mouse phrenic nerve hemidiaphragm (MPN) assay as described by Pearce et al., 1994 (Pearce L B, Borodic G E, First E R, MacCallum R D (1994), Toxicol Appl Pharmacol 128: 69-77) and Habermann et al., 1980 (Habermann E, Dreyer F, Bigalke H. (1980), Naunyn Schmiedebergs Arch Pharmacol. 311:33-40) allow determining the toxic effect of a given neurotoxin preparation on a living organism or an isolated neuromuscular preparation. For establishing the toxic effect in an $LD_{50}$ assay, the neurotoxin must be biologically active in each of said three activities mentioned above. Moreover, various other assays are available, allowing e.g. to determine whether a neurotoxin or the light chain of the neurotoxin is proteolytically active. Such assays are e.g. based on contacting BoNT/A with SNAP-25. Alternatively, a peptide representing the cleavage site of SNAP-25 can be used, wherein the peptide can be labelled to ease detection. In a preferred aspect, biological activity is determined by using the MPN assay described herein above.

A nucleic acid molecule encoding said BoNT/A single-chain protein may be used according to the present invention. Said nucleic acid molecule may optionally comprise regulatory elements. The term "regulatory elements" as used herein refers to regulatory elements of gene expression, including transcription and translation, and includes elements such as tata box, promotor, enhancer, ribosome binding site, Shine-Dalgarno-sequence, IRES-region, polyadenylation signal, terminal capping structure, and the like. Said regulatory element may comprise one or more heterologous regulatory elements or one or more homologous regulatory elements. A "homologous regulatory element" is a regulatory element of a wild-type cell, from which the nucleic acid molecule is derived, which is involved in the regulation of gene expression of the nucleic acid molecule or the polypeptide in said wild-type cell. A "heterologous regulatory element" is a regulatory element which is not involved in the regulation of gene expression of the nucleic acid molecule or the polypeptide in said wild-type cell. Regulatory elements for inducible expression, such as inducible promoters, may also be used.

The nucleic acid molecule can be, for example, hnRNA, mRNA, RNA, DNA, PNA, LNA, and/or modified nucleic acid molecules. The nucleic acid molecule can be circular, linear, integrated into a genome or episomal. Also concatemers coding for fusion proteins comprising three, four, five, six, seven, eight, nine or ten polypeptides are encompassed. Moreover, the nucleic acid molecule may contain sequences encoding signal sequences for intracellular transport such as signals for transport into an intracellular compartment or for transport across the cellular membrane.

According to the invention, a nucleic acid molecule encoding for BoNT/A may be designed to advantageously provide high levels of expression in the host cells, particularly bacterial host cells, preferably *E. coli* cells. Methods of designing nucleic acid molecules to increase protein expression in host cells, particularly bacterial host cells, preferably *E. coli* cells, are known in the art, and include decreasing the frequency (number of occurrences) of "slow codons" in the encoding nucleic acid sequence.

In one aspect, a single-chain BoNT/A protein is produced using an expression vector comprising a nucleic acid molecule encoding said single-chain BoNT/A protein. A vector may be suitable for in vitro and/or in vivo expression of said single-chain BoNT/A protein. The vector can be a vector for transient and/or stable gene expression. The vector may additionally comprise regulatory elements and/or selection markers. Said vector may be of viral origin, of phage origin, or of bacterial origin. For example, said expression vector may be a pET-26b(+) vector.

A nucleic acid molecule or an expression vector encoding a BoNT/A single-chain protein may be comprised in a host cell comprising the nucleic acid molecule or the vector of the present invention. The term "host cell" as used herein, encompasses prokaryotic and/or eukaryotic cells suitable to translate said nucleic acid molecule or said vector and in particular the BoNT/A single-chain protein. Said host cell may be a host cell not expressing the BoNT/A single-chain protein or a homolog thereof. The term "homolog" as used herein refers to a polypeptide comprising a polypeptide sequence having at least 50%, at least 60%, at least 70%, at least 80%, at least 90%, at least 95%, at least 96%, at least 97%, at least 98%, at least 99% or more sequence identity with a BoNT/A sequence, for example the BoNT/A sequence of SEQ ID NO: 1. However, also encompassed are host cells, such as wild-type cells, expressing the BoNT/A single-chain protein or a homolog thereof. For example, a host cell may be selected from *C. botulinum, C. butyricum, C. baratii* and *C. tetani*, such as *C. botulinum* of serotype A, B or F. The host cell may be the Hall strain (ATCC 3502) of *C. botulinum*; the BoNT/A producing strain ATCC 19397, also known as NCTC 4587 and NCTC 7272 of *C. botulinum*; the BoNT/A producing strain NCTC 2916 of *C. botulinum*; the BoNT/A2 producing strain Kyoto-F or Mauritius/NCTC 9837 of *C. botulinum*; the BoNT/A3 producing strain A254 Loch Maree/NCTC 2012 of *C. botulinum*; the BoNT/A4 and B producing strain CDC657 of *C. botulinum*; the BoNT/A5 and B3' producing strain H04402 065 of *C. botulinum*; the BoNT/B1 producing strain Okra/NCTC 7273 of *C. botulinum*; the BoNT/B and F producing strain CDC4013/NCTC 12265 of *C. botulinum*; or the BoNT/F1 producing strain Langeland/NCTC 10281 of *C. botulinum*. Said host cell may be a *Clostridium sporogenes, Clostridium perfringens, Clostridium acetobutylicum, B. cereus, B. thuringiensis, B. mycoidis, B. thermoproteolyticus, B. anthracis, B. megaterium, B. subtilis, E. coli,* or a yeast cell. Preferably the host cell is an *E. coli* host cell, particularly an *E. coli* BL21 (DE3) or BLR(DE3) cell.

In one aspect, the BoNT/A single-chain protein is modified inside the host cell (i.e. glycosylated, phosphorylated, processed by proteases, etc.). Modification also includes the addition of non-proteinaceous co-factors including metal-ions. The host cell may comprise an inducer of expression of the BoNT/A single-chain protein. Such an inducer of expression may be a nucleic acid molecule or a polypeptide or a chemical entity, including a small chemical entity, having the effect of increasing the amount of the BoNT/A single-chain protein in host cell cultures or lysates thereof. The inducer of expression may e.g. increase transcription or translation of a nucleic acid molecule encoding the BoNT/A single-chain protein. The inducer may, for example, be expressed by recombinant means known to the person skilled in the art. Alternatively, the inducer may be isolated from a cell, e.g. a clostridial cell.

A single-chain BoNT/A protein may be produced by a method comprising introducing an expression vector as described herein into and expressing said single-chain BoNT/A protein in said host cell. A single-chain BoNT/A protein may be produced by providing a host cell comprising a nucleic acid encoding said single-chain BoNT/A protein and expressing said single-chain BoNT/A protein in said host cell. Typically the host cell is a bacterial cell, preferably an *E. coli* cell. The *E. coli* host cell may be an *E. coli* BL21 (DE3) or BLR (DE3) cell.

Preferably, the BoNT/A single-chain protein is translated in a cell. The cell may be a prokaryotic or eukaryotic cell. In one aspect the cell is selected from *E. coli, B. subtilis* or yeast; *E. coli* being a highly preferred host cell. Also encompassed by the present invention is the translation of the BoNT/A single-chain protein in a wild-type cell, i.e. a cell isolated from nature, such as any known isolate of *Clostridium botulinum, Clostridium butyricum, Clostridium baratii,* and *Clostridium tetani*. Any suitable host cell as described herein may be used according to the present invention.

Various standard means and methods are available to the skilled person for bringing a nucleic acid molecule or a vector into a host cell and for expressing the BoNT/A single-chain protein as recombinant protein in a cell. Moreover, the skilled person knows many standard techniques for extracting proteins and polypeptides from cells or cell lysates (e.g. Recombinant DNA Principles and Methodologies, J. Green, Marcel Dekker Inc., 1998; The Condensed Protocols: From Molecular Cloning: A Laboratory Manual, Sambrook et al, Cold Spring Harbor Laboratory, 2006; Molecular Cloning: A Laboratory Manual, Sambrook et al., Cold Spring Harbor Laboratory, 2000). Any of these means and methods may be used in the methods of the present invention.

Typical methods of extracting the proteins from a host cell or host cell lysate include centrifugation (clarification) of cell lysate, ammonium sulphate precipitation of proteins, resuspension of proteins, centrifugation of resuspended proteins, ion exchange chromatography, size exclusion chromatography, hydrophobic interaction chromatography and the like. Several combinations of such steps, in differing order, may be useful according to the present invention to purify the BoNT/A single-chain protein.

As described in more detail below, BoNT/A single-chain protein may be contacted with Lys-C to produce the active BoNT/A di-chain. The inventors have now developed an advantageous method for purifying BoNT/A di-chain from the reaction mixture of BoNT/A and Lys-C.

Endoproteinase Lys-C

As described herein, a single-chain BoNT/A protein is cleaved to form the active di-chain form of the BoNT/A protein using endoproteinase Lys-C(Lys-C). The term "Lys-C" refers to the 33 kDa serine endoproteinase Lys-C from *Lysobacter enzymogenes* (Lysyl endopeptidase, LeK, Genbank acc. Q7M135) that specifically cleaves peptide bonds C-terminally to lysine or a homolog thereof having at least 50% sequence identity. In one embodiment, the homolog thereof having at least 50% sequence identity to Lys-C retains the functionality (i.e. proteolytic activity) of Lys-C.

According to the present invention, the Lys-C enzyme is a proteolytically active polypeptide which may comprise or consist of a polypeptide sequence having at least 50% sequence identity with the sequence of SEQ ID NO: 8. In one aspect, the Lys-C enzyme used according to the present invention is a proteolytically active polypeptide consisting of a polypeptide sequence as shown in SEQ ID NO: 8.

Typically, homologs of Lys-C are capable of hydrolysing a single-chain botulinum neurotoxin (e.g. serotype A (BoNT/A)) to produce the di-chain botulinum neurotoxin (e.g. serotype A (BoNT/A)). In one embodiment, the term "Lys-C" also embraces functionally equivalent proteases, such as those proteases that recognise the same cleavage sequence as Lys-C and hydrolyze at the carboxyl side of Lys. Also encompassed by the term are homologs of said protease having at least 60% sequence identity.

The term "proteolytically active polypeptide" as used herein refers to the catalytic function of the polypeptide and means that the polypeptide is capable of hydrolysing a peptide bond. In one aspect, "proteolytically active polypeptide" refers to a polypeptide that is capable of hydrolysing a polypeptide comprising an amino acid sequence selected from any one of SEQ ID NOs: 1 to 7.

The term "proteolytically inactive polypeptide" as used herein refers to the catalytic function of the polypeptide and means that the polypeptide is incapable of hydrolysing a peptide bond.

A skilled person can determine whether a Lys-C polypeptide according to the sequence definition mentioned herein is a polypeptide for use according to the present invention, by testing the proteolytic activity of said polypeptide. An assay or test system for determining proteolytic activity comprises contacting a Lys-C polypeptide which comprises a polypeptide sequence having at least 50% sequence identity with the sequence of SEQ ID NO: 8 with a test substrate.

A test substrate is typically a polypeptide which is known to be cleavable by Lys-C. Preferably, the test substrate is a Clostridial neurotoxin (CNT), such as BoNT or a fragment thereof. The test substrate can be e.g. uncleaved/unprocessed BoNT, designated herein as single-chan BoNT (sc-BoNT) and can be e.g. of serotype A, B, $C_1$, D, E, F or G (e.g. scBoNT/A, scBoNT/B etc.) or the test substrate can be tetanus neurotoxin (TNT). Alternatively, the test substrate can be a fragment of a clostridial neurotoxin, said fragment comprising an amino acid sequence selected from any one of SEQ ID NOs: 1 to 7. The fragment can be a polypeptide of 50 or more amino acid residues or a peptide of up to 49 amino acid residues. As used throughout the present specification, the term "polypeptide" refers to molecules with 50 or more amino acid residues, whereas the term "peptide" refers to molecules with 2 to 49 amino acid residues The test substrate may be a soluble neurotoxin fragment called $LH_N$ comprising the light chain polypeptide, the exposed loop peptide region and the N-terminal half of the heavy chain polypeptide, the translocation domain $H_N$. The test substrate may be or comprise a peptide selected from any one of SEQ ID NOs: 2 to 8 (see Table 1). The test substrate may be a chimeric neurotoxin comprising amino acid residues derived from two or more serotypes.

An assay for determining the proteolytic activity of a Lys-C enzyme, homolog or derivative thereof typically comprises a step of determining the degree of conversion of the test substrate into its cleavage product(s). The observation of one or more cleavage product(s) generated after contacting the polypeptide with the test substrate or the observation of an increase in the amount of cleavage product(s) is indicative of proteolytic activity of the polypeptide. Said step of determining may involve comparing substrate and cleavage product(s). Said comparing may involve determining the amount of substrate and/or the amount of one or more cleavage product(s) and may also involve calculating the ratio of substrate and cleavage product(s). In addition, the assay for determining the proteolytic activity may comprise a step of comparing a test sample with a reference sample, wherein the reference sample typically comprises (a) a polypeptide which comprises a polypeptide sequence having at least 50% sequence identity with the sequence of SEQ ID NO: 8 and which is known to be proteolytically active and (b) a test substrate known to be cleavable by the polypeptide of (a).

The assay for determining the proteolytic activity may comprise separating substrate (e.g. BoNT/A single-chain protein) and cleavage product(s) (e.g. active BoNT/A di-chain) by electrophoresis or by column chromatography and, optionally, a spectrometric analysis. It may be convenient to label the test substrate with one or more labels in order to more easily detect decrease of test substrate and/or increase of product(s). The term "label", as used herein, means a detectable marker and includes e.g. a radioactive label, an antibody and/or a fluorescent label. The amount of test substrate and/or cleavage product may be determined e.g. by methods of autoradiography or spectrometry, including methods based on energy resonance transfer between at least two labels. Alternatively, immunological methods such as western blot or ELISA may be used for detection.

In a preferred aspect, a polypeptide is proteolytically active, if more than 20%, preferably more than 95% of test substrate is converted into the cleavage products such as the light chain and the heavy chain in 120 min at 37° C. using a buffer selected from 100 mM Tris-HCl, pH 8.0 or PBS (50 mM $Na_2HPO_4$, 150 mM NaCl, pH 7.4). The same conditions apply, if the test substrate is not full length BoNT/A but, instead, e.g. a fragment of the full length BoNT/A or a derivative of BoNT/A. It is apparent that the cleavage products will differ in this case. However, the skilled person can quantify the corresponding cleavage products.

Typically, 100 ng of proteolytically active Lys-C polypeptide and a molar ratio of 1:100 with regard to the substrate are used in the assay.

A sample may be taken at intervals in order to follow the catalytic activity over time.

The assay may be modified, e.g. by using multiple amounts of the proteolytically active Lys-C polypeptide.

SEQ ID NO: 9 shows the polypeptide sequence of a proteolytically inactive polypeptide derived from a *Clostridium botulinum* strain ATCC 3502, GenBank accession No: CAL82988.1, having an amino acid length of 581 residues. SEQ ID NO: 8 shows a proteolytically active derivative of SEQ ID NO: 9, lacking amino acid residues 1 to 248 of SEQ ID NO: 9.

The term "polypeptide which comprises a polypeptide sequence having at least 50% sequence identity with the sequence of SEQ ID NO: 8" refers to a polypeptide which has at least 50% sequence identity with the sequence of SEQ ID NO: 8. In addition, the term refers to a polypeptide which comprises a polypeptide sequence having at least 50% sequence identity with the sequence of SEQ ID NO: 8. Said polypeptide may have additional amino acids, for example at an internal position or N- or C-terminal to the sequence shown in SEQ ID NO: 8 or at an internal position or N- or C-terminal to an amino acid sequence which is at least 50% identical with sequence of SEQ ID NO: 8, wherein a methionine may be present at the N-terminus of the polypeptide. In addition, the term refers to a polypeptide lacking one or more amino acid residues, for example at an internal position or at the N- or C-terminus of the sequence shown in SEQ ID NO: 8 or at an internal position or the N- or C-terminus of a sequence which is at least 50% identical in sequence to SEQ ID NO: 8. The term "sequence identity" and means of calculating sequence identity are defined herein in relation to BoNT/A, and the same definitions and means also apply to the discussion of Lys-C.

Typically, sequence identity of the Lys-C enzyme is determined over the entire length of SEQ ID NO: 8 or 9, i.e. over a length of 333aa or 581aa, respectively. The term "at least 50% sequence identity" as used herein means at least 50%, at least 55%, at least 60%, at least 65%, at least 70%, at least 75%, at least 80%, at least 85%, at least 90%, at least 95% or 100% sequence identity.

The proteolytically active Lys-C polypeptide may have the same number of amino acids as the reference polypeptide sequence as shown in SEQ ID NO: 8. Alternatively, the polypeptide may have additional amino acid residues or fewer amino acid residues. For example, the proteolytically active polypeptide of the present invention may consist or comprise of a truncation mutant of SEQ ID NO: 8 or 9 or of a polypeptide having at least 50% sequence identity with the sequence of SEQ ID NO: 8 or 9. The truncation mutant of SEQ ID NO: 9 may for example lack one or more amino acid residues N-terminal to amino acid position 249. A truncation mutant may be an N- or C-terminal truncation mutant and/or an internal truncation mutant that is proteolytically active. The truncation mutant of SEQ ID NO: 9 may lack amino acid positions 1 to 248 of SEQ ID NO: 9. Alternatively, the truncation mutant of SEQ ID NO: 9 may be a C-terminal truncation mutant. The truncation mutant may lack up to 1, 2, 3, 4, 5, 6, 7, 8, 9, 10, 15, 20, 50, 100, 150 or up to 170 consecutive amino acid residues. The proteolytically active polypeptide may have an amino acid length of at least 200 amino acid (aa) residues, of at least 250aa residues, of at least 300aa residues or of at least 333aa residues. Alternatively, the proteolytically active polypeptide may have up to 333aa residues, up to 350aa residues, up to 573 residues, up to 581aa residues, up to 592aa residues, up to 600aa or up to 617aa residues.

The proteolytically active polypeptide may encompass a polypeptide comprising additional amino acid residues at the N- or C-terminus and/or at an internal position of the polypeptide chain of SEQ ID NO: 8 or a of a polypeptide sequence having at least 50% sequence identity with the sequence of SEQ ID NO: 8. These additional amino acid residues may comprise up to 5, up to 10 or even up to 200, 300 or up to 400 consecutive amino acid residues. The additional amino acid residues may function as an inhibitor of the proteolytic activity. These additional amino acid residues may be removed by a protease. Alternatively, additional residues inhibiting the proteolytic activity of the polypeptide are excluded. The additional amino acid residues may be flanked by one or more protease cleavage sites.

In another aspect, the additional amino acid sequence functions as a detectable tag and/or allows binding to a solid support.

In another aspect, the polypeptide chain of SEQ ID NO: 8 or a of a polypeptide sequence having at least 50% sequence identity with the sequence of SEQ ID NO: 8 is modified by exchanging one or more amino acid residues. The term "exchanging", as used herein, means replacing an amino acid with a different amino acid. For example, up to 1 amino acid (aa), 2aa, 3aa, 4aa, 5aa, 6aa, 7aa, Baa, 9aa, 10aa, 15aa, 20aa or up to 50aa may be replaced within the polypeptide sequence. The exchanges may involve conservative or non-conservative amino acid changes, aiming e.g. at increasing or decreasing substrate binding or proteolytic activity of the polypeptide.

Typically the proteolytically active polypeptide encompasses a polypeptide that is capable of hydrolysing a substrate (e.g. single-chain BoNT/A protein) into two or more native cleavage product(s). The polypeptide of the present invention may hydrolyse the substrate into two or more cleavage products which are the same as or differ from the native cleavage products. Preferably the cleavage products are the same as the native cleavage products.

The term "native cleavage products" or "native products" as used herein refers to products, which are identical in amino acid sequence when compared to products generated from the same substrate in wild-type cell cultures, from which the substrate originates. In a preferred embodiment, the cleavage product is the di-chain neurotoxin of a botulinum neurotoxin or of tetanus neurotoxin. In a more preferred embodiment the di-chain neurotoxin is a neurotoxin isolated from C. botulinum of serotype A, B, C1, D, E, F or G. In yet another aspect, said di-chain neurotoxin is a native di-chain BoNT/A neurotoxin.

It is to be understood that the definitions and explanations of the terms made above and below apply mutatis mutandis for all aspects described in this specification unless otherwise indicated.

Methods of BoNT Production

The present invention relates to the use of Lys-C in a method for proteolytically processing a polypeptide, specifically a BoNT/A single-chain protein, and a means of purifying the active-BoNT/A di-chain produced from the Lys-C using hydrophobic interaction chromatography (HIC). In one aspect, the present invention relates to a method for the manufacture of an active BoNT/A di-chain, comprising the step of contacting: (a) Lys-C with (b) a BoNT/A single-chain protein, said BoNT/A single-chain protein being susceptible to proteolysis by Lys-C, wherein said contacting results in proteolytic processing of said BoNT/A single-chain protein into at least two cleavage products, preferably including the active BoNT/A di-chain, and purifying said active di-chain using HIC.

The method of the invention can be used to manufacture proteolytically processed clostridial neurotoxin (CNT) or botulinum neurotoxin (BoNT), specifically proteolytically processed BoNT/A, i.e. the active BoNT/A di-chain, as described herein. Using the method of the present invention, it is now possible to obtain active BoNT/A di-chain compositions with significantly less contamination by unprocessed or partially processed BoNT/A, since those contaminants are efficiently processed into di-chain BoNT/A. The methods of the present invention also allow effective removal of the Lys-C enzyme used to process the single-chain BoNT/A protein into the active di-chain, i.e. improved purification of the active BoNT/A di-chain.

Thus, the present invention relates to purification (resolution) of the BoNT/A di-chain from Lys-C comprises separation by hydrophobic interaction chromatography. Accordingly, the invention provides a method for producing a di-chain BoNT/A protein, comprising providing a single-chain BoNT/A protein, contacting said BoNT/A protein with endoproteinase Lys-C in solution and separating the BoNT/A protein from the Lys-C by contacting the solution containing the BoNT/A protein and Lys-C with a hydrophobic surface, wherein the BoNT/A protein preferentially binds to the hydrophobic surface. Typically, contacting the single-chain BoNT/A protein with Lys-C results in cleavage of the single-chain BoNT/A protein into a soluble di-chain form. Preferably, the cleavage product of the single-chain BoNT/A protein by Lys-C is the same as the native BoNT/A cleavage product. Typically, both the single-chain and di-chain forms of BoNT/A are soluble.

One or more fractions collected from a chromatography column can be concentrated e.g. by precipitation or ultrafiltration.

In one embodiment, wherein the invention provides a method (as described above) for producing soluble di-chain BoNT/A protein, the soluble single-chain BoNT/A protein is provided by a method as described above for producing soluble single-chain BoNT/A protein in a host cell, preferably a bacterial host cell, most preferably an E. coli host cell.

Any suitable expression system may be used to produce the soluble single-chain BoNT/A protein. An expression system according to the present invention may be an in vivo or an in vitro (cell-free) expression system. Examples of suitable in vivo and in vitro expression systems are known in the art. As defined herein, an expression system may comprise a suitable host cell and/or a suitable expression vector for use in said host cell. For example, a suitable expression system may comprise a bacterial host cell and/or an expression vector suitable for expressing the soluble single-chain BoNT/A protein in said bacterial host cell.

The single-chain BoNT/A protein may be produced in any suitable host cell as described herein, such as a bacterial cell. Typically an *Escherichia coli* (*E. coli*) host cell is used. The single-chain BoNT/A protein may be produced by a method comprising: expressing a nucleic acid sequence in a host cell (e.g an *E. coli* cell) expression system. Such expression can involve introducing a nucleic acid molecule encoding said single-chain BoNT/A protein into said host cell, and translating said nucleic acid molecule to produce single-chain BoNT/A protein. Methods and techniques used to express heterologous proteins in expression systems, including *E. coli* expression systems, are well known in the art.

Typically, said soluble single-chain BoNT/A protein is expressed in the cytoplasm of said *E. coli* host cell.

The soluble single-chain BoNT/A protein may be expressed at a level (concentration) of at least 5 mg/L (for example, at least 5, 6, 7, 8, 9, 10, 15, 20, 25, 30, 25, 40, 45, 50, 60, 70, 80, 90, 100, 200, 300, 400 or 500 mg/L, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 15 mg/mL, 20 mg/mL, 25 mg/mL, 50 mg/mL, 100 mg/mL or more). Typically the expression level of single-chain BoNT/A protein refers to the level of single-chain BoNT/A in a cell culture. In one embodiment, said expression level refers to the crude host cell (e.g. bacterial host cell) homogenate, i.e. a crude homogenate of the host cells (e.g. bacterial host cells) used to express the single-chain BoNT/A protein. Thus, in one embodiment, the expression level of single-chain BoNT/A protein in the crude host cell homogenate, for example the crude bacterial host cell homogenate, is at least 5 mg/L (as defined herein).

The method for producing soluble single-chain BoNT/A protein, as described above, may comprise lysis of the host cell, preferably a bacterial host cell, most preferably an *E. coli* host cell to provide a host cell homogenate, more preferably a bacterial host cell homogenate, most preferable an *E. coli* host cell homogenate containing said soluble single-chain BoNT/A protein. Methods and techniques used to lyse host cells, such as bacterial cells, particularly *E. coli* host cells, are known in the art. Examples include ultrasonication or the use of a French press.

Purification of *C. botulinum* or *E. coli* expressed BoNT/A single-chain protein may be done e.g. as essentially described in the prior art (DasGupta 1984, Toxicon 22, 415; Sathyamoorthy 1985, J Biol Chemistry 260, 10461). In particular, purification of the neurotoxin can contain one or more precipitation and extraction steps, one or more concentration steps, and further distinct chromatographic steps. Recombinant single chain BoNT/A and its purification is described in prior art (Rummel et al., 2004, Mol Microbiol. 51:631-43).

The bacterial host cell used to produce the BoNT/A single-chain protein, or a derivative thereof, may be *C. botulinum* or *E. coli*. For fermentation, the process described by DasGupta B. R. et al. in Toxicon, vol. 22, No. 3, p. 414 to 424, 1984, can be used. Therefore 0.5% yeast extract and 0.6% autoclaved yeast paste is added to 2% of the N-Z-amine type A medium, and a pH of 7.2 will be adjusted with the help of 4 M NaOH, and the medium prepared in such a way will afterwards be autoclaved. To this medium separately autoclaved glucose (20% by weight per volume) may be added, to come to a final concentration of glucose of 0.5% in the medium. Incubation may occur e.g. at 37° C. without stirring, wherein the fermentation is discontinued e.g. after 96 hours. Batch fermentation, semi-batch fermentation, repeated batch fermentation or continuous fermentation may be used.

After the actual fermentation and separation of the fermentation medium from the cells the fermentation medium may undergo a first precipitation with the goal of removing large proteins. The precipitation is preferably an acid precipitation. Reaction conditions for such an acid precipitation are known to those skilled in the art. Typically 1.5 M $H_2SO_4$ may be used, to acidify the supernatant to a pH of 3.5. The centrifugation usually occurs for 20 minutes at 2400×g at 4° C. The pellet received through centrifugation may be washed with water, preferably repeatedly. Subsequently, the pellet may be extracted with a 0.1 M citric acid-trisodium citrate buffer, pH 5.5 e.g. for an hour. Subsequently, a further centrifugation step may be performed, e.g. at 9800×g for 20 minutes at 4° C. The so obtained pellet optionally can then again be extracted as described before. The supernatant of the extraction, and both supernatants in case of repetition of the extraction, may then be subjected to protamine sulphate precipitation. The precipitation may continue overnight, e.g. at 8° C. Subsequently, the precipitate may be centrifuged, e.g. for 20 minutes at 4° C. and at 12,000×g. The supernatant of centrifugation may be subject to a precipitation such as an ammonium sulphate precipitation, whereby other larger proteins can be removed. After the ammonium sulphate precipitation step another centrifugation step may be added and subsequently the so obtained pellet may be redissolved and, optionally, be subjected to a dialysis. The extract which is preferably dialysed and centrifuged again, can be subjected to a succession of chromatography steps with the objective of purifying the neurotoxin. Each of the chromatography steps serves to remove contaminants such as protamine sulphate, remaining DNA, parts of smaller proteins and middle-sized proteins as well as the hemagglutinins of the botulinum neurotoxin protein complex. For this purpose, one or more chromatography steps may be used in a preferred embodiment. Optionally, the eluate of, e.g. the last chromatography step, may be filtrated in order to remove micro-organisms. Optionally the eluate can be diluted before filtration and suitable adjuvants can be added. During further steps another sterile filtration may be carried out after addition of the adjuvants. In one aspect, the filtration is carried out in reaction containers which may then be subject to a step of lyophilization.

The BoNT/A single-chain protein may be contacted with Lys-C after it has been isolated from the host cell or host cell lysate and then subjected to the method of the present invention.

When the single-chain BoNT/A protein of the invention is contacted with Lys-C, the proteolytic action of Lys-C cleaves the single-chain protein at a site between the L-chain protease component and the translocation component to produce a di-chain protein, where the two chains are linked by a disulphide bridge. For example, the two chains formed following cleavage of single-chain BoNT/A1, A2 and A4-A6 at the activation site are a first chain of amino acid residues 1-438 and a second chain of amino acid residues 449-1296 (except in A6, wherein the second chain has amino acid residues 449-1297), with residues 439-447 removed by the cleavage event. The two chains formed following cleavage of single-chain BoNT/A3 at the activation site are a first chain of amino acid residues 1-434 and a second chain of amino acid residues 445-1292, with residues 435-444 removed by the cleavage event. Thus, Lys-C can be used to activate the single-chain polypeptide by converting it to the active di-chain form. Advantageously, therefore, the use of Lys-C means that it is not necessary to engineer an exogenous (non-native) cleavage site into a BoNT/A, and also enables the production of the native BoNT/A di-chain.

In one embodiment, reference to Lys-C embraces Lys-C-like and variant enzymes that cleave at the same protease cleavage site as Lys-C, as described herein.

The term "contacting" as used herein refers to bringing at least two different compounds in physical proximity as to allow physical and/or chemical interaction of said compounds. In accordance with the method of this invention, the said two different compounds are, a BoNT/A single-chain protein and Lys-C, which are comprised in a solution. Contacting is carried out under conditions and for a time being sufficient to allow interaction of the BoNT/A single-chain protein and Lys-C.

The term "being susceptible to proteolysis" refers to a feature or requirement of the BoNT/A single-chain protein and is used herein meaning that said BoNT/A single-chain protein is proteolytically cleavable by Lys-C. In other words, the term "being susceptible to proteolysis" means that the BoNT/A single-chain protein comprises a protease recognition and cleavage site allowing it to function as a substrate of the Lys-C. As described herein, the BoNT/A single-chain protein is a substrate of Lys-C and is proteolytically processed into two or more cleavage products (preferably just two peptides—the L-chain or fragment thereof and H-chain or fragment thereof joined together via a disulphide bond). Using the assay described herein above, the skilled person can test whether a given BoNT/A single-chain protein is a substrate of the first polypeptide and, thus, a "second polypeptide" according to present invention's definition. The term "at least two cleavage products" includes, for example, up to two, three, four, five and up to six cleavage products.

This method can be used, for example, for preparing a pharmaceutical composition comprising a BoNT/A di-chain or for generating polypeptide fragments used in a method of mass spectrometry. The Lys-C and the BoNT/A single-chain protein can be contacted at various steps in the manufacturing process of the BoNT/A di-chain. For example, the step of contacting the Lys-C and the BoNT/A single-chain protein may be within a cell, such as by expression of Lys-C and BoNT/A single-chain protein in said cell.

Alternatively, said step of contacting is in a cell lysate or in a purified cell lysate. This encompasses adding the Lys-C to the lysate or the purified lysate. The Lys-C can be added at various steps during purification of the BoNT/A single-chain protein from the cell lysate. For example, the Lys-C can be added prior to or after: protein precipitation, ion exchange chromatography, hydrophobic interaction chromatography and/or size exclusion chromatography.

The step of contacting requires incubation at conditions and for a time sufficient for the Lys-C to cleave the BoNT/A single-chain protein. Exemplary conditions can comprise adding a buffer selected from the group consisting of 100 mM Tris-HCl, pH 8.0 or PBS (50 mM $Na_2HPO_4$, 150 mM NaCl, pH 7.4). Preferred buffer conditions include 100 mM Tris-HCl, pH 8.0. The "time sufficient to cleave" can be determined using the assay described herein above. In one aspect, said "time sufficient to cleave" depends on the degree of cleavage that the proteolytically processed polypeptide or a composition comprising it should have. In one aspect, the method comprises a step of incubating the Lys-C and the BoNT/A single-chain protein for at least 30 min, 60 min, 120 min or at least 240 min. In another aspect, the Lys-C and BoNT/A single-chain protein are incubated for up to 30 min, 60 min, 120 min, 240 min, 480 min or up to 600 min. In another aspect, the method comprises a step of incubating the Lys-C and the BoNT/A single-chain protein at 4° C. or at 37° C. In another aspect, the method comprises a step of incubating for up to 1 h, up to 2 h, 4 h, 6 h, 10 h or up to 16 h.

In one embodiment, wherein the invention provides a method (as described above) for producing soluble di-chain BoNT/A protein, the method comprises separating the soluble BoNT/A protein from the Lys-C by contacting the solution containing soluble BoNT/A protein and Lys-C with a hydrophobic surface, wherein the soluble BoNT/Lys-C protein preferentially binds to the hydrophobic surface.

The present inventors have found that high yields of activated di-chain BoNT/A protein can be obtained by using a process of hydrophobic purification to separate the activated di-chain polypeptide from Lys-C. Surprisingly, this process provides superior purification to standard purification using ion exchange chromatography, which the present inventors have found to be less effective for separating the activated di-chain polypeptide from Lys-C. In addition, the process advantageously provides an activated di-chain BoNT/A protein that is free from the activating protease and thus suitable for use in therapy, as part of a general purification process.

As described herein, the production of active recombinant BoNT/A requires a proteolytic step that cleaves the molecule into the active di-chain form. This cleavage can be achieved by an in vitro activation step using the endoproteinase Lys-C. After the activation step, it is important to remove the Lys-C from the final product, which also prevents any further non-specific cleavage of BoNT/A.

As shown in Table 2 below, the calculated isoelectric points (pI) of Lys-C and BoNT/A are 6.70 and 6.05 respectively, which indicates that separation of the two proteins should be achieved by Ion Exchange (IEX) chromatography, exploiting the charge difference between the two molecules. A protein's net charge is affected by the pH of its surrounding environment and will become more positively or negatively charged depending on whether it gains or loses protons. The pI is the pH value at which a molecule carries no electrical charge and will therefore not interact with a charged IEX medium. This means that if a protein is at a pH above its pI then it will carry a net negative charge and will bind to a positively charged medium such as an anion exchanger. Similarly, if the buffer pH is below the pI then the protein will carry a net positive charge and will not bind to an anion exchanger.

Furthermore, as illustrated in Table 2, BoNT/A and Lys-C have similar mean hydropathicities, but large charge differences at pHs 4.5 and 8.0. Based on this principle, it would be expected that ion exchange chromatography (IEX) could be used to resolve (separate) BoNT/A and Lys-C. IEX is a simple and inexpensive chromatography method, as it does not require the protein loaded onto the column to be in a high salt buffer, which can lead to protein losses by precipitation.

The present inventors have tested a variety of anion exchange columns, using both strong and weak functional groups attached to cross-linked agarose beads, at pH 8. When compared to the elution of BoNT/A it was found that, unexpectedly, Lys-C eluted at a similar ionic strength (Table 3; FIGS. 7 to 10) indicating that Lys-C was not separated as predicted and would be present in the final purified BoNT/A product with the additional possibility of further BoNT/A degradation.

The present inventors have solved the above problem. In more detail, the inventors have surprisingly identified that optimal Lys-C-BoNT/A separation is achieved by use of a hydrophobic separation surface (for example, by hydrophobic interaction chromatography (HIC), which separates proteins according to differences in their surface hydrophobicity by utilising a reversible interaction between these proteins and the hydrophobic surface of a HIC matrix/resin).

Typically, the active BoNT/A di-chain preferentially binds to the hydrophobic surface of the HIC resin/matrix (these terms are used interchangeable herein) compared with Lys-C binding to the hydrophobic surface. "Preferential" binding may be defined as increased or improved binding of the active BoNT/A di-chain to the hydrophobic surface compared with the binding of Lys-C to the hydrophobic surface. For example, the active BoNT/A di-chain may bind to the hydrophobic surface with at least two times, three times, four times, five times, six times, seven times, eight times, nine times, ten times, 15 times, 20 times, 25 times, 30 times, 40 times, 50 times, 100 times or greater the affinity of Lys-C to the hydrophobic surface. In a preferred embodiment, the active BoNT/A di-chain binds to the hydrophobic surface with at least five times, or at least ten times the affinity of Lys-C to the hydrophobic surface.

In one embodiment, the hydrophobic surface is an inert matrix/resin to which a ligand comprising or consisting of aryl or alkyl groups is attached.

The term "aryl" refers to aromatic groups, for example phenyl, naphthyl, thienyl, and indolyl.

The term "alkyl" refers to aliphatic groups including straight-chain, branched-chain, cyclic groups, and combinations thereof. An alkyl group may have 1 to 12 carbon atoms. Examples of alkyl groups include, but are not limited to groups such as methyl, ethyl, propyl (e.g. n-propyl, isopropyl), butyl (e.g. n-butyl, isobutyl, sec-butyl, t-butyl), pentyl, hexyl, heptyl, and octyl.

In one embodiment, the hydrophobic surface comprises one or more ligand selected from the group consisting of: butyl, phenyl or octyl ligands.

In one embodiment, the hydrophobic surface comprises butyl ligands. In one embodiment, the hydrophobic surface comprises phenyl ligands. In one embodiment, the hydrophobic surface comprises octyl ligands.

The hydrophobic surface may contain any suitable inert matrix/resin with an appropriate hydrophobic ligand attached. For example, the inert matrix/resin may be selected from silica, crosslinked dextran, crosslinked polyacrylamide or crosslinked agarose and the like. Also included are in particular polypeptides, glass, polystyrene, polypropylene, polyethylene, polyethylene glycol (PEG), dextran, nylon, amylases, natural and modified celluloses, polyacrylamides, gabbros, and magnetite. The inert matrix is, for example, a polysaccharide matrix selected from the group consisting of: sepharose, sephadex, agarose, sephacell, micro-cellulose, and alginate-beads. In another aspect, said inert matrix/resin can consist of glass-beads, and/or polypeptide matrices.

The inert matrix/resin can have any suitable structural configuration or arrangement. For example, the matrix/resin may be spherical, as in a bead, or cylindrical, as in the inside surface of a test tube, or the external surface of a rod. Alternatively, the matrix may be irregular or flat such as a sheet or test strip.

Figure 2:
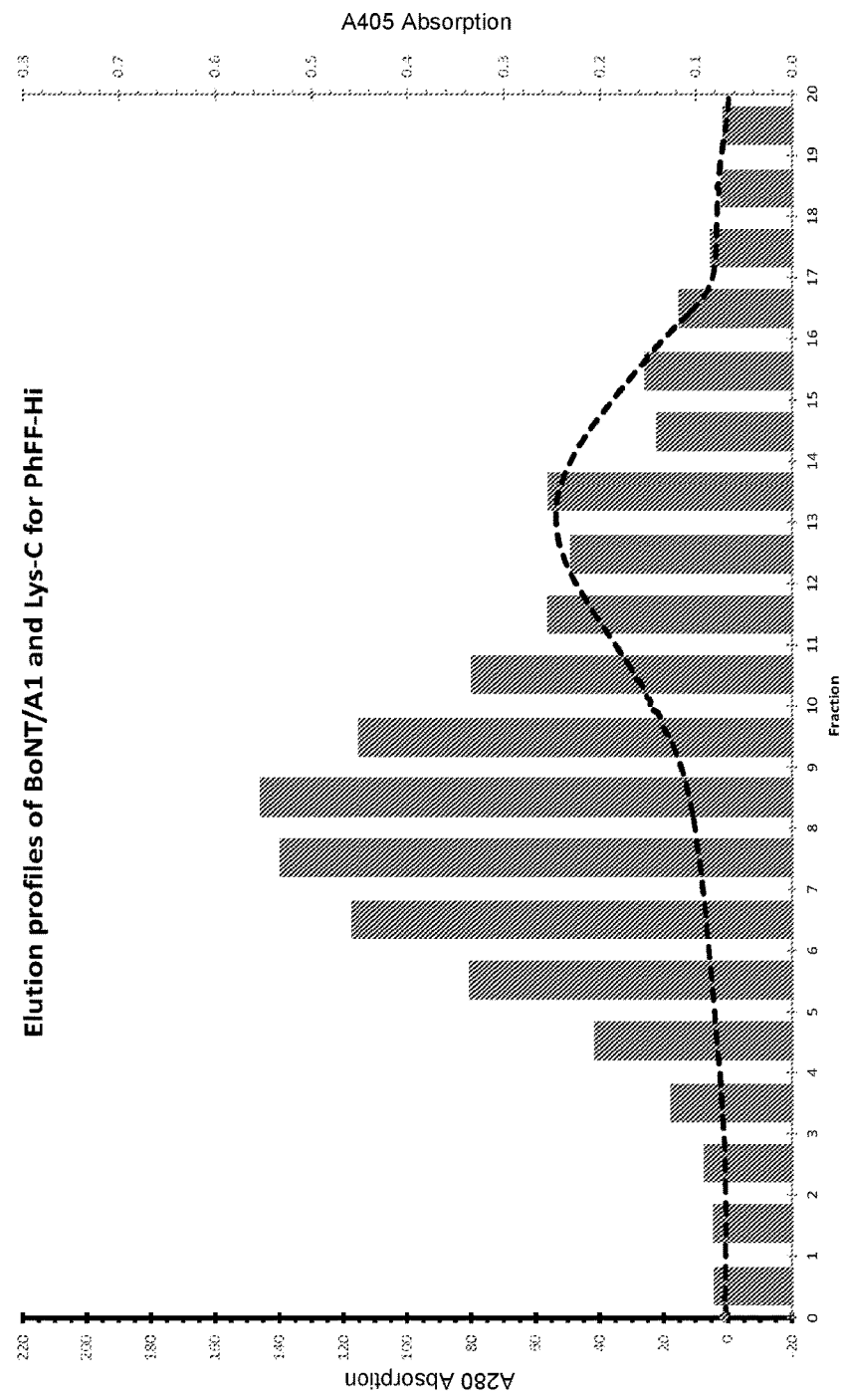
Figure 3:
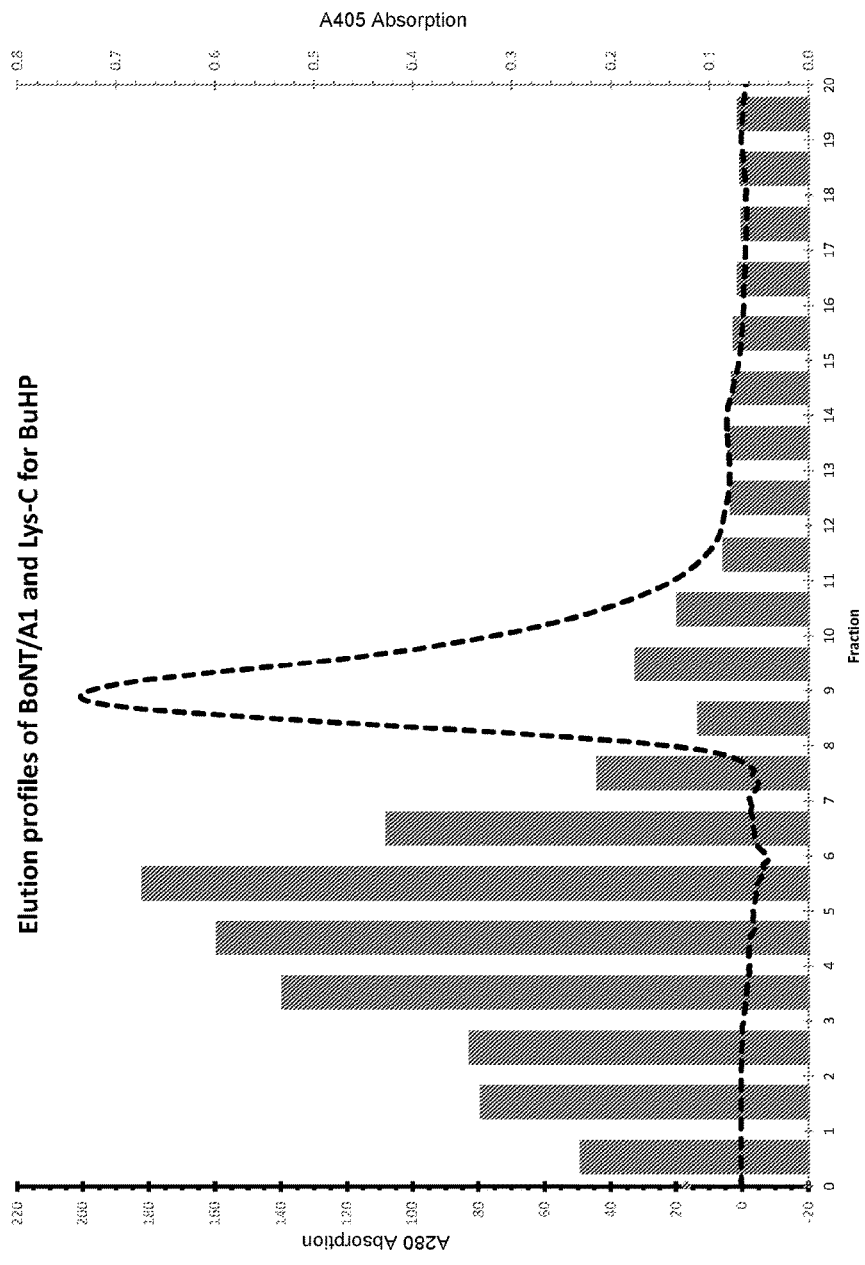

The present inventors have discovered that particularly preferable results for separating Lys-C from BoNT/A are obtained with HIC using chromatography matrices/resins containing alkyl or aryl groups, for example butyl, phenyl, and octyl ligands, coupled to an inert matrix/resin, such as cross-linked agarose or polystyrene beads (Table 4; FIGS. 1 to 3).

The use of HIC provides improved resolution of Lys-C from active BoNT/A di-chain compared with ion exchange chromatography (IEX).

"Fast flow" HIC chromatography resins/matrices may be used according to the present invention. A "Fast flow" resin/matrix may be defined as a resin/matrix with a more uniform average particle size than a standard HIC resin/matrix and will use smaller particles. Specifically, a "Fast flow" resin/matrix will have a more narrow range of smaller particle sizes. Particle size may be quantified in any appropriate way known in the art, for example in terms of average particle diameter. Typically, a "Fast flow" resin/matrix will comprise particles (e.g. beads) of an average diameter of less than 100 µm, less than 95 µm, less than 90 µm or less. In a preferred embodiment, the average diameter of a "Fast flow" resin/matrix is less than 90 µm. Typically, the average particle spread of a "Fast flow" resin/matrix will be from about 20 to about 180 µm, from about 30 to about 170 µm, from about 40 to about 170 µm, from about 40 to about 165 µm. In a preferred embodiment, the average particle spread of a "Fast flow" resin/matrix is from about 44 to about 165 µm.

In a preferred embodiment, high performance HIC resins are used, such as Phenyl High Performance (PhHP) or Butyl High Performanc (BuHP) resins. Such high performance HIC matrices/resins typically provide improved resolution of Lys-C from active BoNT/A di-chain compared with ion exchange chromatography (IEX), even when high performance IEX matrices/resins, such as Quaternary amine High Performance (QHP) matrix/resin, are used. As discussed herein, the major difference between high performance resins/matrices and others is that the average particle size (again, this may be quantified in any appropriate way known in the art, for example average particle diameter) is smaller (34 μm vs. 90 μm) and more uniform (24-44 μm vs. 44-165 μm), resulting in improved resolution.

A high performance HIC resin/matrix typically has a more uniform average particle size than a standard HIC resin/matrix, or even a "Fast flow" resin/matrix as defined herein and will use smaller particles. Specifically, a high performance HIC resin/matrix will have a more narrow range of smaller particle sizes than a standard HIC resin/matrix, or even a "Fast flow" resin/matrix as defined herein.

Thus, the invention provides the use of high performance HIC resins/matrices. Typically, a high performance HIC resin/matrix has an average particle diameter of less than 70 μm, less than 60 μm, less than 50 μm, less than 40 μm, less than 30 μm or less. In a preferred embodiment, a high performance HIC resin/matrix has an average particle diameter of less than 40 μm, more preferable less than 35 μm, e.g. 34 μm.

Typically, the average particle spread of a high performance HIC resin/matrix will be from about 10 to about 60 μm, from about 10 to about 50 μm, from about 20 to about 50 μm, from about 20 to about 44 μm. In a preferred embodiment, the average particle spread of a high performance resin/matrix is from about 22 to about 44 μm.

Typically, the process of hydrophobic purification to separate the activated di-chain BoNT/A protein from Lys-C reduces the concentration of Lys-C at least two-fold, at least 5-fold, at least 10-fold, at least 15-fold, at least 20-fold, at least 25-fold, at least 30-fold, at least 35-fold, at least 40-fold, at least 45-fold, or at least 50-fold. In a preferred embodiment, the process of hydrophobic purification to separate the activated di-chain BoNT/A protein from Lys-C reduces the concentration of Lys-C at least 10-fold.

The ability of hydrophobic purification to separate the activated di-chain BoNT/A from Lys-C may also be quantified in terms of the percentage of the Lys-C contained in the starting solution comprising the activated di-chain BoNT/A and Lys-C that remains after the hydrophobic purification step. Typically, less than 80%, 70%, less than 60%, less than 50%, less than 45%, less than 40%, less than 35%, less than 30%, less than 25%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, or less, including 0% of the Lys-C remains in the BoNT/A di-chain product after the hydrophobic purification step. Preferably, less than 50%, more preferably less than 25%, even more preferably less than 10% of the Lys-C remains in the BoNT/A di-chain product after the hydrophobic purification step.

In a related aspect, the invention provides an active di-chain BoNT/A protein obtainable by a method (as described above) for producing soluble di-chain BoNT/A protein.

In one aspect, the invention provides a composition comprising an active di-chain BoNT/A protein (as described above), wherein said composition is substantially free from Lys-C.

Thus, the composition is, advantageously, substantially free from Lys-C protease (used to activate the single-chain polypeptide by converting it to the active di-chain form), thus preventing unwanted non-specific cleavage of BoNT/A protein.

Wherein the composition (as described above) is substantially free from Lys-C, the composition typically contains less than 400 picograms (pg) Lys-C per 100 ng of BoNT/A protein; for example, less than 400, 350, 300, 250, 200, 150, 100, 90, 80, 70, 60, 50, 40, 30, 20, 10, 9, 8, 5, 4, 3, 2, 1 pg or less Lys-C per 100 ng of BoNT/A protein. In one embodiment, the composition (as described above) contains less than 400 pg Lys-C per 100 ng of BoNT/A protein, less than 350 pg Lys-C per 100 ng of BoNT/A protein, less than 300 pg Lys-C per 100 ng of BoNT/A protein, less than 250 pg Lys-C per 100 ng of BoNT/A protein, less than 200 pg Lys-C per 100 ng of BoNT/A protein, less than 150 pg Lys-C per 100 ng of BoNT/A protein, less than 100 pg Lys-C per 100 ng of BoNT/A protein, less than 50 pg Lys-C per 100 ng of BoNT/A protein, less than 40 pg Lys-C per 100 ng of BoNT/A protein, less than 30 pg Lys-C per 100 ng of BoNT/A protein, less than 20 pg Lys-C per 100 ng of BoNT/A protein, less than 15 pg Lys-C per 100 ng of BoNT/A protein, less than 14 pg Lys-C per 100 ng of BoNT/A protein, less than 13 pg Lys-C per 100 ng of BoNT/A protein, less than 12 pg Lys-C per 100 ng of BoNT/A protein, less than 11 pg Lys-C per 100 ng of BoNT/A protein, less than 10 pg Lys-C per 100 ng of BoNT/A protein, less than 9 pg Lys-C per 100 ng of BoNT/A protein, less than 8 pg Lys-C per 100 ng of BoNT/A protein, less than 7 pg Lys-C per 100 ng of BoNT/A protein, less than 6 pg Lys-C per 100 ng of BoNT/A protein, less than 5 pg Lys-C per 100 ng of BoNT/A protein, or less. In a preferred embodiment, the composition (as described above) contains less than 100 pg Lys-C per 100 ng of BoNT/A protein or less than 50 pg Lys-C per 100 ng of BoNT/A protein, less than 20 pg Lys-C per 100 ng of BoNT/A protein, less than 15 pg Lys-C per 100 ng of BoNT/A protein or less than 10 pg Lys-C per 100 ng of BoNT/A protein.

Methods for determining the concentration of Lys-C in a composition are known in the art. By way of example, the concentration of Lys-C in a composition of the invention may be determined using a sandwich ELISA (Enzyme-Linked Immunosorbent Assay) or a colorimetric assay as described herein.

Pharmaceutical Compositions and Therapeutic Indications

The present invention also relates to a composition obtainable by the present invention's method for the manufacture of a BoNT/A di-chain. In one aspect, said composition comprises a mixture of processed (di-chain) and unprocessed (single-chain) BoNT/A, wherein said mixture may contain less than 5%, 4%, 3%, 2% or less than 1% unprocessed (single-chain) BoNT/A. In an aspect of said composition, references to BoNT/A encompass a derivative thereof as defined herein. The composition can be e.g. a liquid or a solid composition and may contain one or more carrier, adjuvants and/or excipients.

In another aspect, the present invention also relates to a method for the manufacture of a medicament, i.e. a pharmaceutical composition, comprising the steps of the aforementioned method and the further step of formulating the purified di-chain BoNT/A as medicament. Typically said medicament comprises a mixture of processed (di-chain) and unprocessed (single-chain) BoNT/A, wherein said mixture contains less than 20%, less than 15%, less than 10%, less than 5% or less unprocessed (single-chain) BoNT/A. In a preferred embodiment, the mixture contains less than 5% unprocessed (single-chain) BoNT/A, such as less than 5%, less than 4%, less than 3%, less than 2% or less than 1% unprocessed (single-chain) BoNT/A.

The present invention also relates to various medical and aesthetic (cosmetic) uses of the compounds and compositions disclosed herein. Accordingly, the present invention relates to an active BoNT/A di-chain or a composition comprising an active BoNT/A di-chain according to the present invention for use as a medicament or in a pharmaceutical composition. The present invention also relates to the use of an active BoNT/A di-chain or a composition comprising an active BoNT/A di-chain of the present invention in the manufacture of a medicament. The present invention also relates to an active BoNT/A di-chain or a composition comprising an active BoNT/A di-chain of the present invention for use in a method of treatment of the human or animal body by therapy. The present invention also relates to a method of treatment comprising administration of an active BoNT/A di-chain or a composition comprising an active BoNT/A di-chain of the present invention to a patient in need thereof.

The term "composition" as used herein refers to any composition formulated in solid, liquid, aerosol (or gaseous) form and the like. Said composition comprises e.g. a therapeutically active compound of the invention optionally together with suitable auxiliary compounds such as diluents or carriers or further ingredients. In one aspect, the therapeutically active compound is the active BonT/A di-chain of the present invention. The compositions, particularly the pharmaceutical compositions, of the invention are typically substantially free of Lys-C as defined herein.

Thus, the present invention provides a solid or liquid pharmaceutical composition comprising:
(a) an active di-chain BoNT/A protein as described above, and
(b) a stabilising agent.

In one embodiment, the composition (as described above) is substantially free from Lys-C. For example, the composition (as described above) may contain less than 400 pg Lys-C per 100 ng of BoNT/A protein, less than 300 pg Lys-C per 100 ng of BoNT/A protein, less than 200 pg Lys-C per 100 ng of BoNT/A protein, less than 100 pg Lys-C per 100 ng of BoNT/A protein, less than 50 pg Lys-C per 100 ng of BoNT/A protein, less than 20 pg Lys-C per 100 ng of BoNT/A protein, less than 15 pg Lys-C per 100 ng of BoNT/A protein, or less than 10 pg Lys-C per 100 ng of BoNT/A protein.

Stabilising agents which can be used in compositions according to the invention include protein stabilisers, such as albumin, in particular human serum albumin (HSA), and non-protein stabilisers.

Non-protein stabilising agents which can be used in the composition according to the invention include surfactants, in particular non-ionic surfactants. Examples of non-ionic surfactants include polysorbates, such as polysorbate 20 or polysorbate 80, and block copolymers such as poloxamers (i.e. copolymers of polyethylene and propylene glycol).

In a particular embodiment, the composition does not comprise a protein as a stabilising agent.

According to a particular embodiment of the invention, the pharmaceutical composition is a liquid pharmaceutical composition comprising:
(a) an active di-chain BoNT/A protein, as described above;
(b) a non-protein stabilising agent that is a surfactant; and
(c) water;
wherein said liquid pharmaceutical composition does not comprise a protein stabilising agent; and
wherein said liquid pharmaceutical composition is substantially free from Lys-C, wherein "substantially free from Lys-C" is as defined herein (e.g. said liquid pharmaceutical composition contains less than 400 pg Lys-C per 100 ng of BoNT/A protein, less than 300 pg Lys-C per 100 ng of BoNT/A protein, less than 200 pg Lys-C per 100 ng of BoNT/A protein, less than 100 pg Lys-C per 100 ng of BoNT/A protein, less than 50 pg Lys-C per 100 ng of BoNT/A protein, less than 20 pg Lys-C per 100 ng of BoNT/A protein, less than 15 pg Lys-C per 100 ng of BoNT/A protein, or less than 10 pg Lys-C per 100 ng of BoNT/A protein).

In one embodiment, the active di-chain BoNT/A protein is present in the composition (as described above) at a concentration of 1-1000 ng/ml or more. Thus, the active di-chain BoNT/A protein may be present in the composition (as described above) at a concentration of about 1-500 ng/mL, e.g. about 1, 5, 10, 15, 20, 25, 30, 35, 40, 45, 50, 100, 150, 200, 250, 300, 350, 400, 450, 500, 550, 600, 650, 700, 750, 800, 850, 900, 950 or 1000 ng/mL or more. In a preferred embodiment, the active di-chain BoNT/A protein is present at a concentration of about 100 ng/mL, 200 ng/mL, 300 ng/mL, 400 ng/mL, 500 ng/mL, 600 ng/mL or 700 ng/mL.

In one embodiment, the surfactant (as described above) is a polysorbate, such as a polysorbate having a mean polymerisation degree ranging from 20 to 100 monomer units, and may for example be polysorbate 80. In a preferred embodiment, the polysorbate is vegetable-derived. The concentration of the surfactant is preferably lower than 1% v/v, for example from about 0.005% to 0.02% v/v in the case of polysorbate 80.

The pharmaceutical composition according to the invention can also comprise a crystalline agent.

By crystalline agent is meant an agent which, inter alia, maintains a mechanically strong cake structure to a lyophilised botulinum neurotoxin complex (type A, B, $C_1$, D, E, F or G) or a high purity botulinum neurotoxin (type A, B, $C_1$, D, E, F or G). When included in solid formulations, crystalline agents also have a bulking effect. Crystalline agents notably include sodium chloride. The concentration of crystalline agent can be for example from 0.1 to 0.5 M, preferably from 0.1 to 0.4 M, notably about 0.15 to 0.3 M.

The pharmaceutical composition according to the invention can also comprise a buffer to maintain pH a level comprised between 5.5 and 7.5, or between 6.0 and 7.0. The buffer can be any buffer able to maintain the adequate pH. For example, the buffer for compositions according to the invention can be chosen from the group consisting of succinate, disodium phosphate/citric acid, and an amino acid such as histidine. The concentration of the buffer can be for example from 1 to 50 mM, preferably from 5 to 20 mM, preferably about 10 mM.

The pharmaceutical composition according to the invention can also comprise a disaccharide.

The disaccharide used in compositions according to the invention can be chosen from the group consisting of sucrose, trehalose, mannitol and lactose. In a specific embodiment, the disaccharide is sucrose. The concentration of the disaccharide can be for example from 5 to 50 mM, preferably from 5 to 25 mM, more preferably from 10 to 20 mM, and most preferably about 11.7 mM.

In a particular embodiment, the pharmaceutical composition is a liquid pharmaceutical composition comprising:
(a) an active di-chain BoNT/A protein, as described above;
(b) a non-protein stabilising agent that is a surfactant;
(c) sodium chloride, (d) a buffer to maintain pH between 5.5 and 7.5
(e) a disaccharide, and
(f) sterile water.
   wherein said liquid pharmaceutical composition does not comprise a protein stabilising agent; and
   wherein said liquid pharmaceutical composition is substantially free from Lys-C, wherein "substantially free from Lys-C" is as defined herein (e.g. said liquid pharmaceutical composition contains less than 400 pg Lys-C per 100 ng of BoNT/A protein, less than 300 pg Lys-C per 100 ng of BoNT/A protein, less than 200 pg Lys-C per 100 ng of BoNT/A protein, less than 100 pg Lys-C per 100 ng of BoNT/A protein, less than 50 pg Lys-C per 100 ng of BoNT/A protein, less than 20 pg Lys-C per 100 ng of BoNT/A protein, less than 15 pg Lys-C per 100 ng of BoNT/A protein, or less than 10 pg Lys-C per 100 ng of BoNT/A protein).

According to a specific embodiment, the pharmaceutical composition according to the invention in liquid form is sealed in a vial or in a ready-to-use device, such as a syringe, with no liquid/gaseous interface, and is stable for at least three months or at least six months at 23 to 27° C. and for at least twelve months at 2-8° C. Exemplary pharmaceutical compositions of the invention are described in the Examples.

The monthly degradation rates for pharmaceutical compositions or formulations of the invention may be below 5% per month over 12 weeks, which means that the di-chain BoNT protease function of the compositions or formulations remains stable at 25° C. for at least 12 weeks.

Pharmaceutical compositions of the present invention can be stored in lyophilized, vacuum dried form in containers under vacuum pressure or as stable liquids. Prior to lyophilization the active di-chain BoNT/A protein can be combined with pharmaceutically acceptable excipients, stabilizers and/or carriers, such as albumin. The lyophilized material can be reconstituted with saline or water to create a solution or composition containing the active di-chain BoNT/A protein to be administered to a patient.

In this context, it is distinguished for the present invention between auxiliary compounds, i.e. compounds which do not contribute to the effects elicited by the compound of the present invention upon application of the composition for its desired purpose, and further ingredients, i.e. compounds which contribute a further effect or modulate the effect of the compound of the present invention. Suitable diluents and/or carriers depend on the purpose for which the composition is to be used and the other ingredients. The person skilled in the art can determine such suitable diluents and/or carriers without further ado.

The carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatine, agar, pectin, acacia, magnesium stearate, stearic acid and the like. Exemplary of liquid carriers are phosphate buffered saline solution, syrup, oil, water, emulsions, various types of wetting agents, and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are selected so as not to affect the biological activity of the combination. Examples of such diluents are distilled water, physiological saline, Ringer's solutions, dextrose solution, and Hank's solution, in addition, the pharmaceutical composition or formulation may also include other carriers, adjuvants, or non-toxic, non-therapeutic, non-immunogenic stabilisers and the like.

In one aspect, a pharmaceutical composition as used herein comprises the biologically active neurotoxin obtained by the method of the present invention (i.e. active BoNT/A di-chain), optionally, one or more pharmaceutically acceptable carrier. The active neurotoxin can be present in liquid or lyophilized form. In an aspect, said compound can be present together with glycerol, protein stabilisers (e.g., human serum albumin (HSA)) or non-proteinaceous stabilisers such as polyvinylpyrrolidone or hyaluronic acid. The pharmaceutical composition is, in one aspect, administered topically.

Conventionally used drug administration is via intramuscular or subcutaneous (typically near sebaceous glands) administration. However, depending on the nature and the mode of action of a compound the pharmaceutical composition may be administered by other routes as well. The di-chain neurotoxin polypeptide is the active ingredient of the composition, and is in one aspect administered in conventional dosage forms prepared by combining the drug with standard pharmaceutical carriers according to conventional procedures. These procedures may involve mixing, granulating, and compression, or dissolving the ingredients as appropriate to the desired preparation. It will be appreciated that the form and character of the pharmaceutical acceptable carrier or diluent is dictated by the amount of active ingredient with which it is to be combined, the route of administration, and other well-known variables.

A therapeutically effective dose refers to an amount of the compound, the neurotoxin, to be used in a pharmaceutical composition of the present invention which prevents, ameliorates or treats the symptoms accompanying a disease or condition referred to in this specification. Therapeutic efficacy and toxicity of the compound can be determined by standard pharmaceutical procedures in cell cultures or experimental animals, e.g., ED50 (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$.

The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. The pharmaceutical compositions and formulations referred to herein are administered at least once in order to treat or ameliorate or prevent a disease or condition recited in this specification. However, the said pharmaceutical compositions may be administered more than one time.

As described herein, the active di-chain BoNT/A proteins of the invention, and the compositions and liquid pharmaceutical compositions thereof, can be used in therapy. Suitable therapies may include cosmetic treatments and methods of medical treatment.

In a further aspect of the invention, the aforementioned composition is a medicament or a cosmetic composition. In one aspect the said medicament comprising the biologically active neurotoxin (i.e. active BoNT/A di-chain) can be used for prevention and/or treatment of at least one of the following diseases and disorders: voluntary muscle strength, focal dystonia, including cervical, cranial dystonia, and benign essential blepharospasm, hemifacial spasm, and focal spasticity, gastrointestinal disorders, hyperhidrosis, and cosmetic wrinkle correction, in a further aspect also blepharospasm, oromandibular dystonia, jaw opening type, jaw closing type, bruxism, Meige syndrome, lingual dystonia, apraxia of eyelid, opening cervical dystonia, antecollis, retrocollis, laterocollis, torticollis, pharyngeal dystonia, laryngeal dystonia, spasmodic dysphonia/adductor type, spasmodic dysphonia/abductor type, spasmodic dyspnea, limb dystonia, arm dystonia, task specific dystonia, writer's cramp, musician's cramp, golfer's cramp, leg dystonia, thigh adduction, thigh abduction knee flexion, knee extension, ankle flexion, ankle extension, equinovarus, deformity foot dystonia, striatal toe, toe flexion, toe extension, axial dystonia, pisa syndrome, belly dancer dystonia, segmental dystonia, hemidystonia, generalised dystonia, dystonia in lubag, dystonia in corticobasal degeneration, dystonia in lubag, tardive dystonia, dystonia in spinocerebellar ataxia, dystonia in Parkinson's disease, dystonia in Huntington's disease, dystonia in Hallervorden Spatz disease, dopa-induced dyskinesias/dopa-induced dystonia, tardive dyskinesias/tardive dystonia, paroxysmal dyskinesias/dystonias, kinesiogenic non-kinesiogenic action-induced palatal myoclonus, myoclonus myokymia, rigidity, benign muscle cramps, hereditary chin trembling, paradoxic jaw muscle activity, hemimasticatory spasms, hypertrophic branchial myopathy, maseteric hypertrophy, tibialis anterior hypertrophy, nystagmus, oscillopsia supranuclear gaze palsy, epilepsia, partialis continua, planning of spasmodic torticollis operation, abductor vocal cord paralysis, recalcitrant mutational dysphoria, upper oesophageal sphincter dysfunction, vocal fold granuloma, stuttering Gilles de Ia Tourette syndrome, middle ear myoclonus, protective larynx closure, postlaryngectomy, speech failure, protective ptosis, entropion sphincter Odii dysfunction, pseudoachalasia, nonachalsia, oesophageal motor disorders, vaginismus, postoperative immobilisation tremor, bladder dysfunction, detrusor sphincter dyssynergia, bladder sphincter spasm, hemifacial spasm, reinnervation dyskinesias, cosmetic use craw's feet, frowning facial asymmetries, mentalis dimples, stiff person syndrome, tetanus prostate hyperplasia, adipositas, treatment infantile cerebral palsy strabismus, mixed paralytic concomitant, after retinal detachment surgery, after cataract surgery, in aphakia myositic strabismus, myopathic strabismus, dissociated vertical deviation, as an adjunct to strabismus surgery, esotropia, exotropia, achalasia, anal fissures, exocrine gland hyperactivity, Frey syndrome, Crocodile Tears syndrome, hyperhidrosis, axillar palmar plantar rhinorrhea, relative hypersalivation in stroke, in Parkinson's, in amyotrophic lateral sclerosis spastic conditions, in encephalitis and myelitis autoimmune processes, multiple sclerosis, transverse myelitis, Devic syndrome, viral infections, bacterial infections, parasitic infections, fungal infections, in hereditary spastic paraparesis postapoplectic syndrome hemispheric infarction, brainstem infarction, myelon infarction, migraine, in central nervous system trauma, hemispheric lesions, brainstem lesions, myelon lesion, in central nervous system hemorrhage, intracerebral hemorrhage, subarachnoidal hemorrhage, subdural hemorrhage, intraspinal hemorrhage, in neoplasias, hemispheric tumors, brainstem tumors, myelon tumors, snoring (WO 2000/033863). For details and symptoms see, e.g., Jost 2007, Drugs 67(5), 669 or Dressler 2000 in Botulinum Toxin Therapy, Thieme Verlag, Stuttgart, N.Y.

In another aspect of the invention, the composition is a cosmetic composition which can be formulated as described for a pharmaceutical composition above. For a cosmetic composition, likewise, it is envisaged that the compound of the present invention is in an aspect used in substantially pure form. Cosmetic compositions are, in a further aspect, to be applied intramuscular. In an even further aspect of the invention, cosmetic compositions comprising the neurotoxin can be formulated as an anti-wrinkle solution.

All references cited in this specification are herewith incorporated by reference with respect to their entire disclosure content and the disclosure content specifically mentioned in this specification.

Key to SEQ ID NOs

SEQ ID NO: 1 BoNT/A of ATCC 3502, Genbank acc. "AAA23262"
SEQ ID NO: 2: Activation loop of BoNT/A1
SEQ ID NO: 3: Activation loop of BoNT/A2/A6
SEQ ID NO: 4: Activation loop of BoNT/A3
SEQ ID NO: 5: Activation loop of BoNT/A3
SEQ ID NO: 6: Activation loop of BoNT/A4
SEQ ID NO: 7: Activation loop of BoNT/A5
SEQ ID NO: 8: Proteolytically active polypeptide derived from a *Clostridium botulinum* strain ATCC 3502, GenBank accession No: "CAL82988.1", lacking 248 N-terminal amino acid residues
SEQ ID NO:9: Proteolytically inactive polypeptide derived from a *Clostridium botulinum* strain ATCC 3502, GenBank accession No: "CAL82988.1"
SEQ ID NO: 10: Nucleic acid sequence encoding SEQ ID NO: 8
SEQ ID NO: 11: Nucleic acid sequence encoding SEQ ID NO: 9
SEQ ID NO: 12: "Streptag" amino acid sequence
SEQ ID NO: 13: Activation loop of BoNT/A7
SEQ ID NO: 14: Activation loop of BoNT/A8
SEQ ID NO: 15: Amino acid sequence of a single chain, recombinant, cationic, botulinum neurotoxin sub-serotype A1 derivative (mrBoNT/A1)

LIST OF FIGURES

FIG. 1: Elution profiles from Phenyl High Performance (PhHP) column on which the separation of Lys-C($A_{405}$—bars) from BoNT/A was assessed ($A_{280}$—dotted line).

FIG. 2: Elution profiles from Phenyl Fast Flow High substitution (PhFF-Hi) column on which the separation of Lys-C($A_{405}$—bars) from BoNT/A was assessed ($A_{280}$—dotted line).

FIG. 3: Elution profiles from Butyl High Performance (BuHP) column on which the separation of Lys-C($A_{405}$—bars) from BoNT/A was assessed ($A_{280}$—dotted line).

Figure 4:
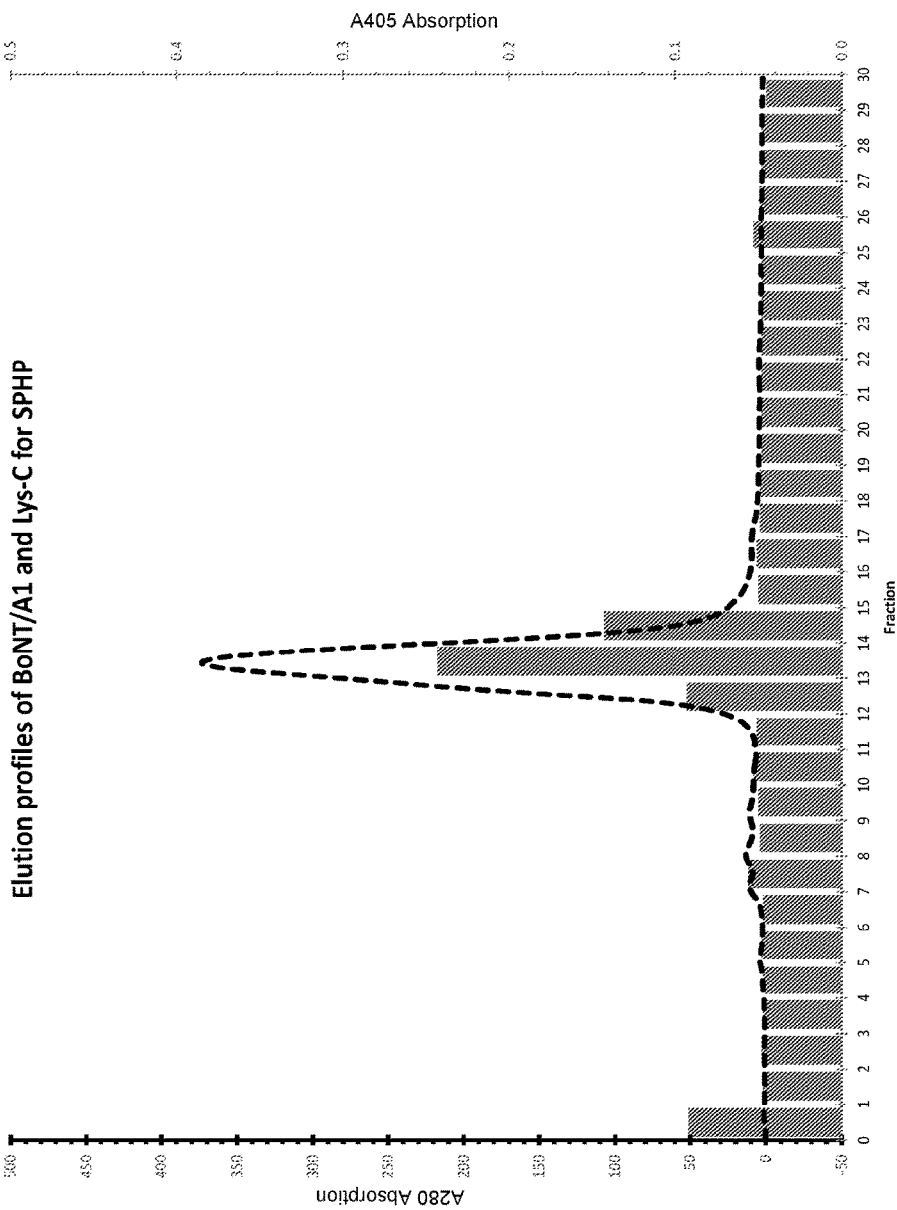

FIG. 4: Elution profiles from Sulphopropyl High Performance (SPHP) column on which the separation of Lys-C ($A_{405}$—bars) from BoNT/A was assessed ($A_{280}$—dotted line).

Figure 5:
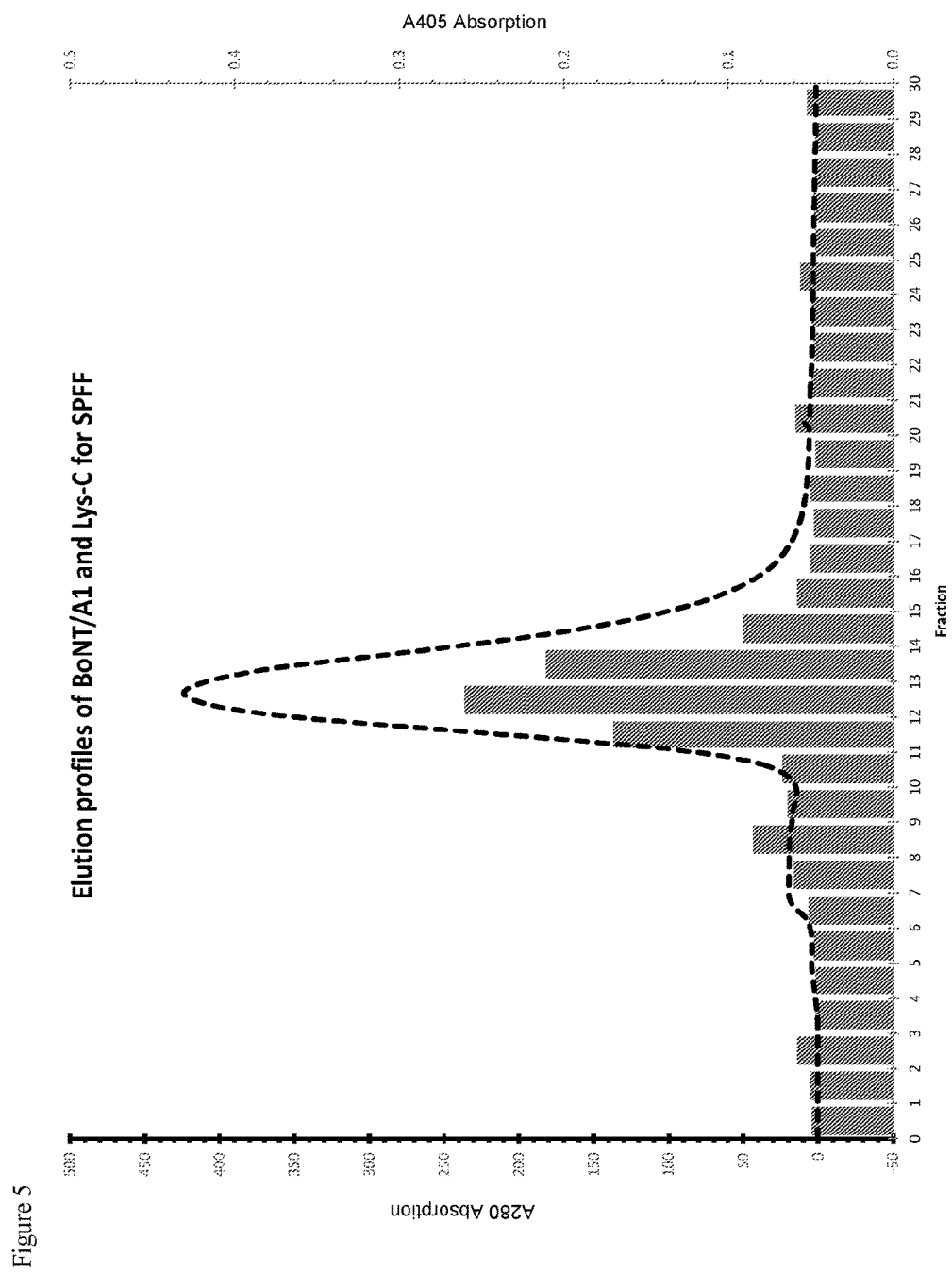

FIG. 5: Elution profiles from Sulphopropyl Fast Flow (SPFF) column on which the separation of Lys-C($A_{405}$—bars) from BoNT/A was assessed ($A_{280}$—dotted line).

Figure 6:
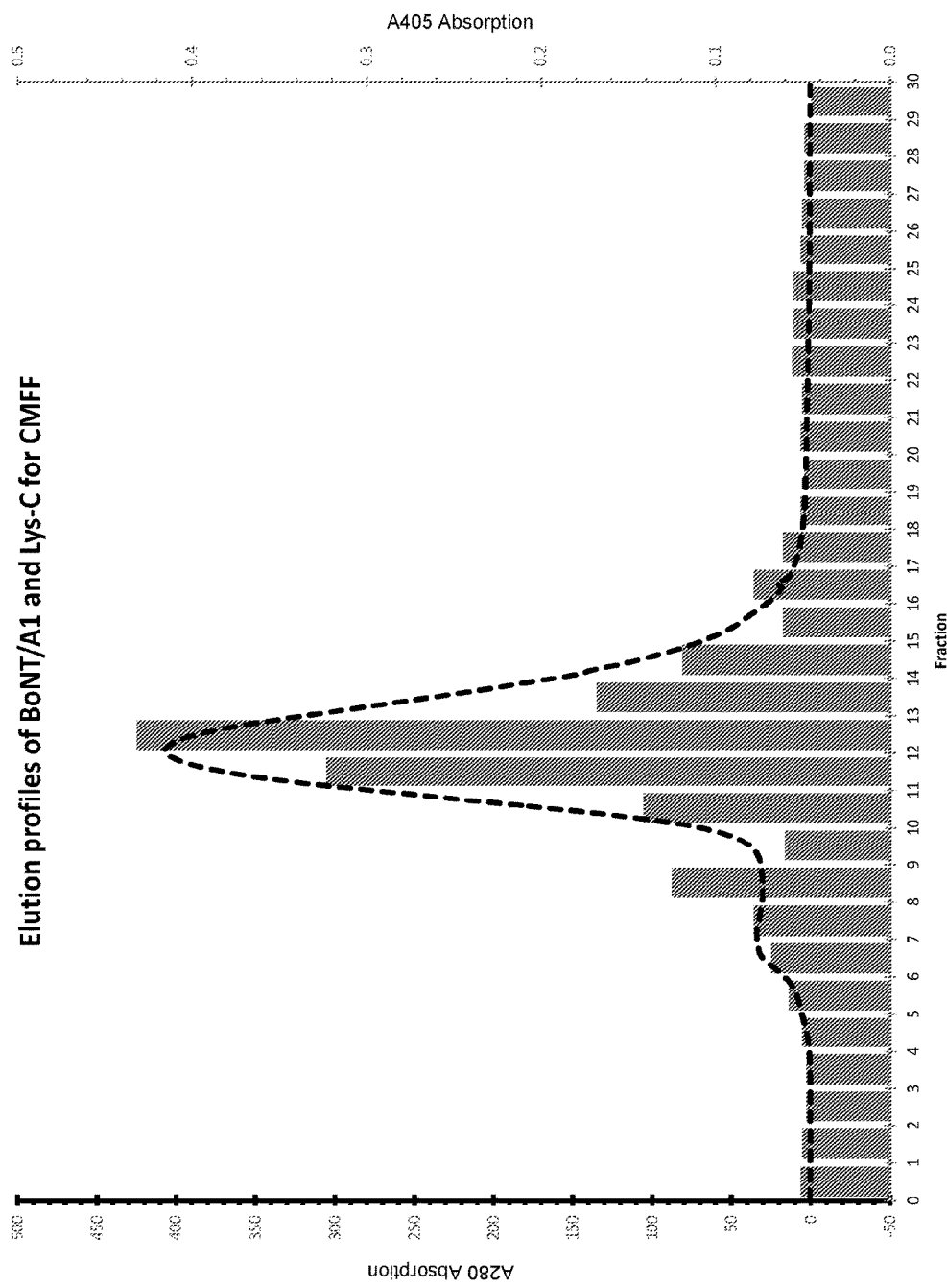

FIG. 6: Elution profiles from Carboxylmethyl Fast Flow (CMFF) column on which the separation of Lys-C($A_{405}$—bars) from BoNT/A was assessed ($A_{280}$—dotted line).

Figure 7:
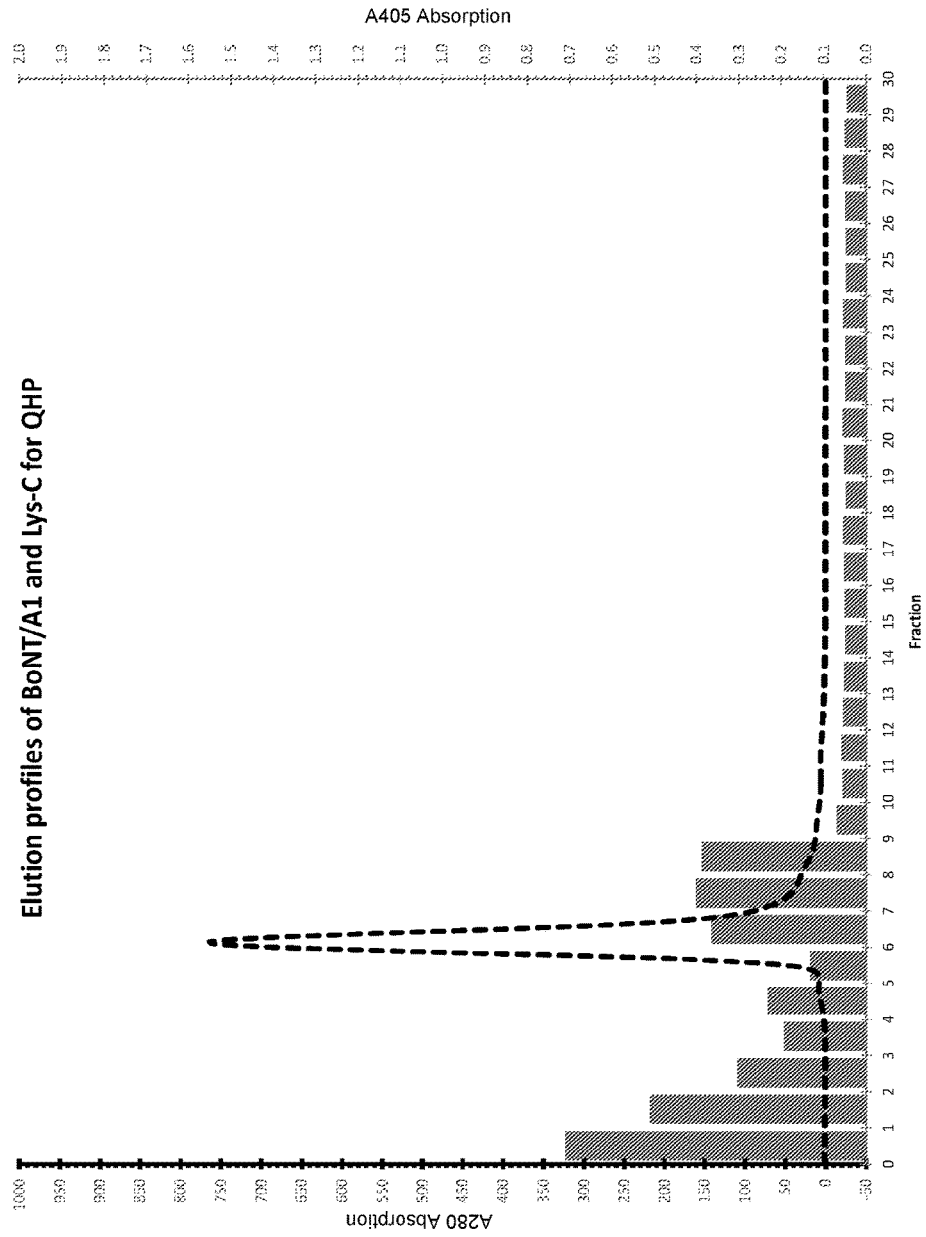

FIG. 7: Elution profiles from Quaternary amine High Performance (QHP) column on which the separation of Lys-C($A_{405}$—bars) from BoNT/A was assessed ($A_{280}$—dotted line).

Figure 8:
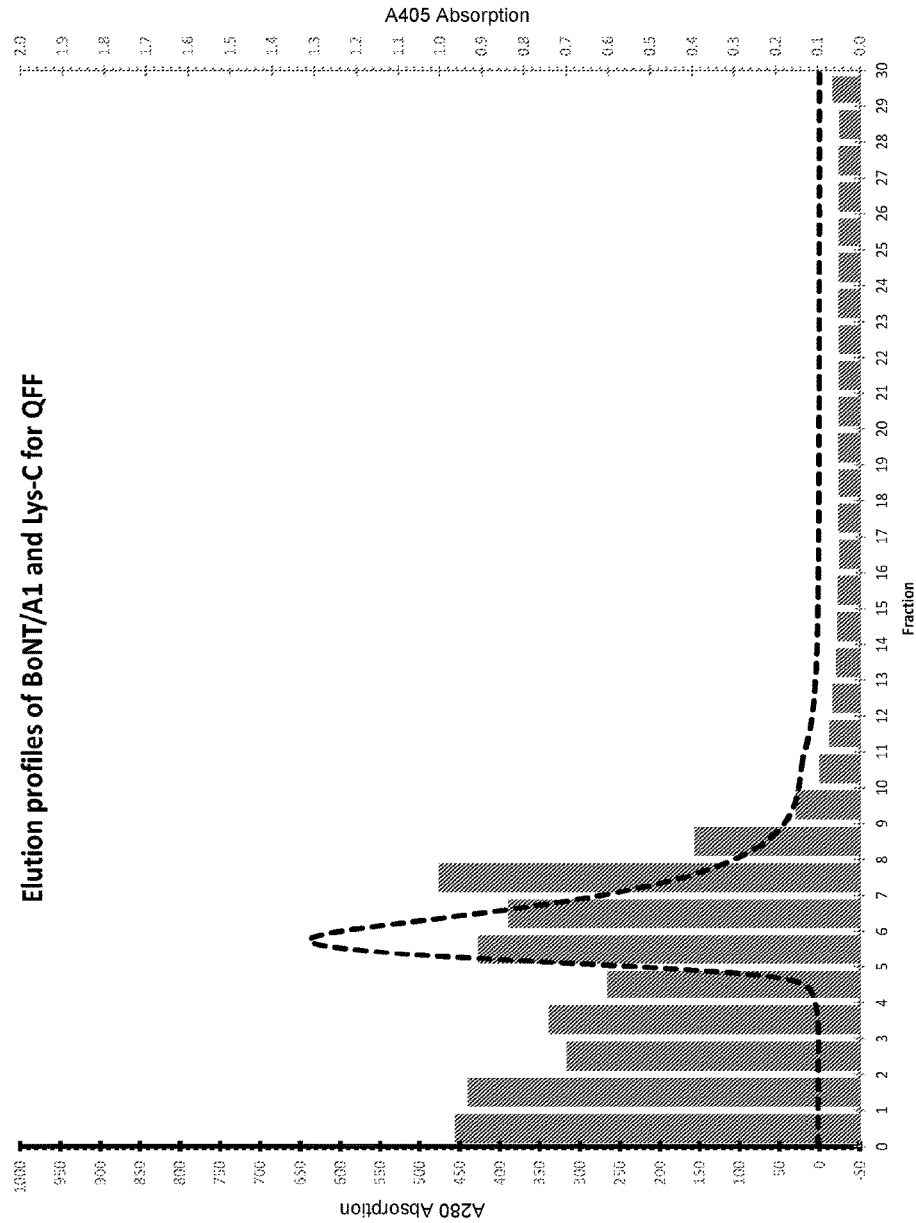

FIG. 8: Elution profiles from Quaternary amine Fast Flow (QFF) column on which the separation of Lys-C($A_{405}$—bars) from BoNT/A was assessed ($A_{280}$—dotted line).

Figure 9:
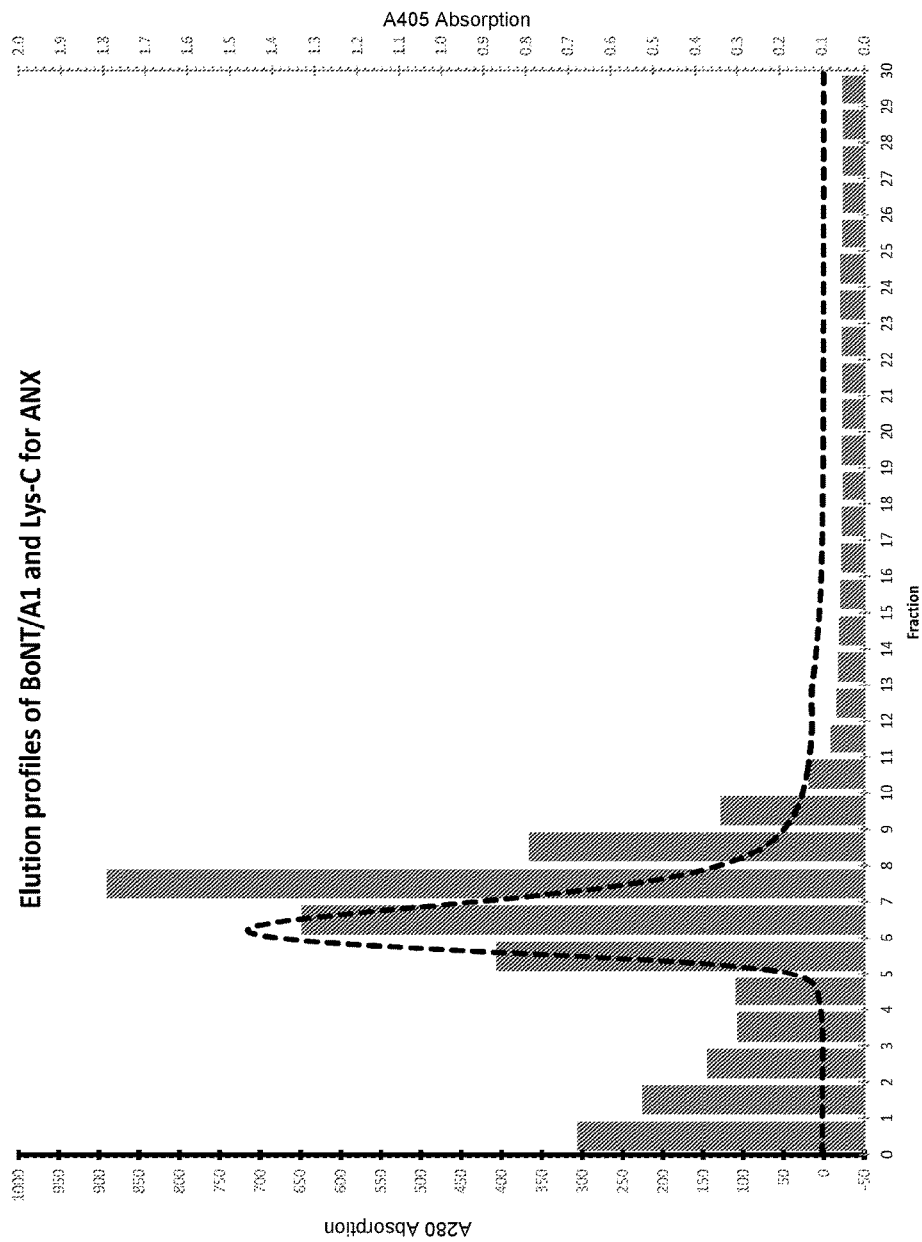

FIG. 9: Elution profiles from Diethylaminopropyl (DEAP, "ANX") column on which the separation of Lys-C($A_{405}$—bars) from BoNT/A was assessed ($A_{280}$—dotted line).

Figure 10:
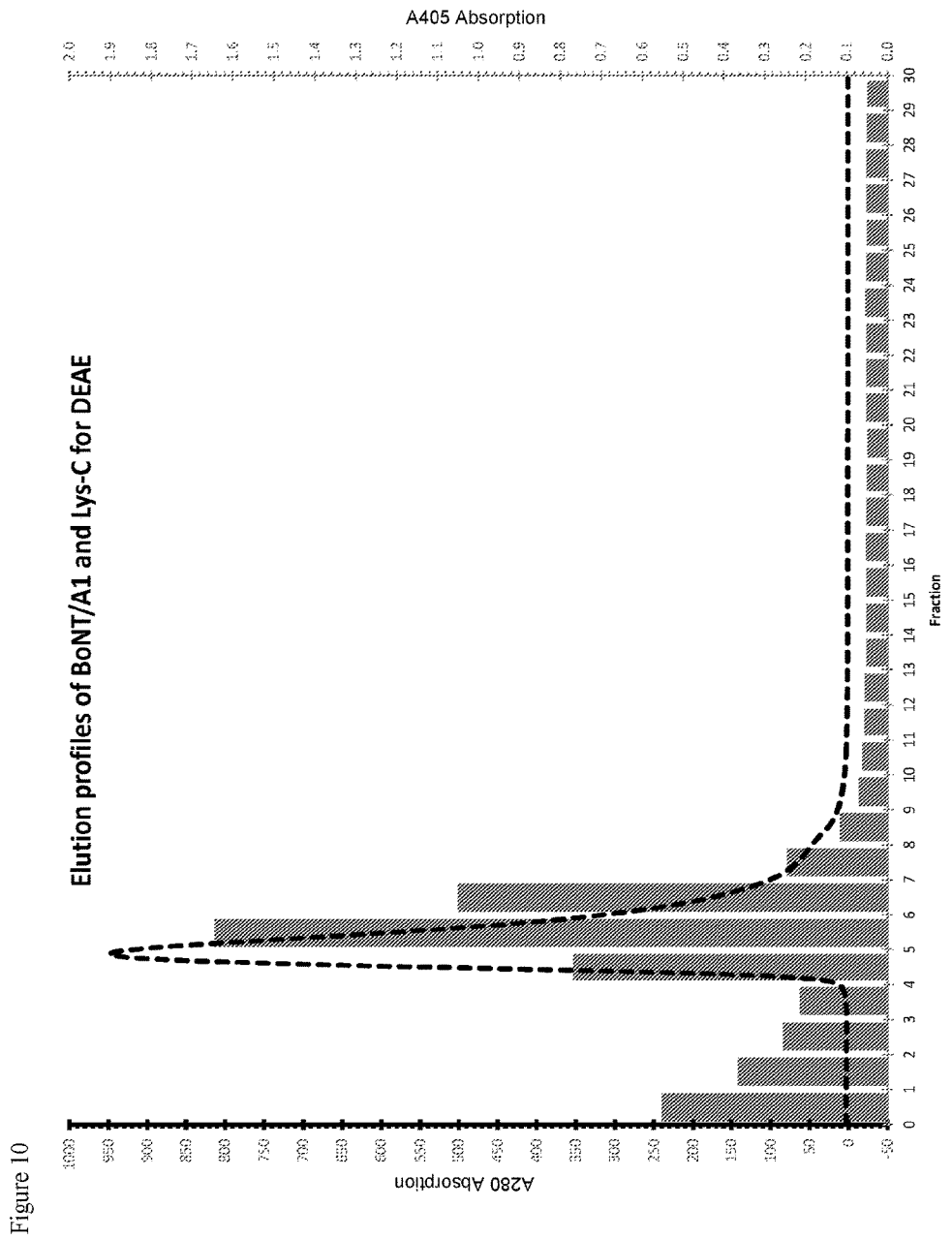

FIG. 10: Elution profiles from Diethylaminoethyl (DEAE) column on which the separation of Lys-C($A_{405}$—bars) from BoNT/A was assessed ($A_{280}$—dotted line).

Figure 11:
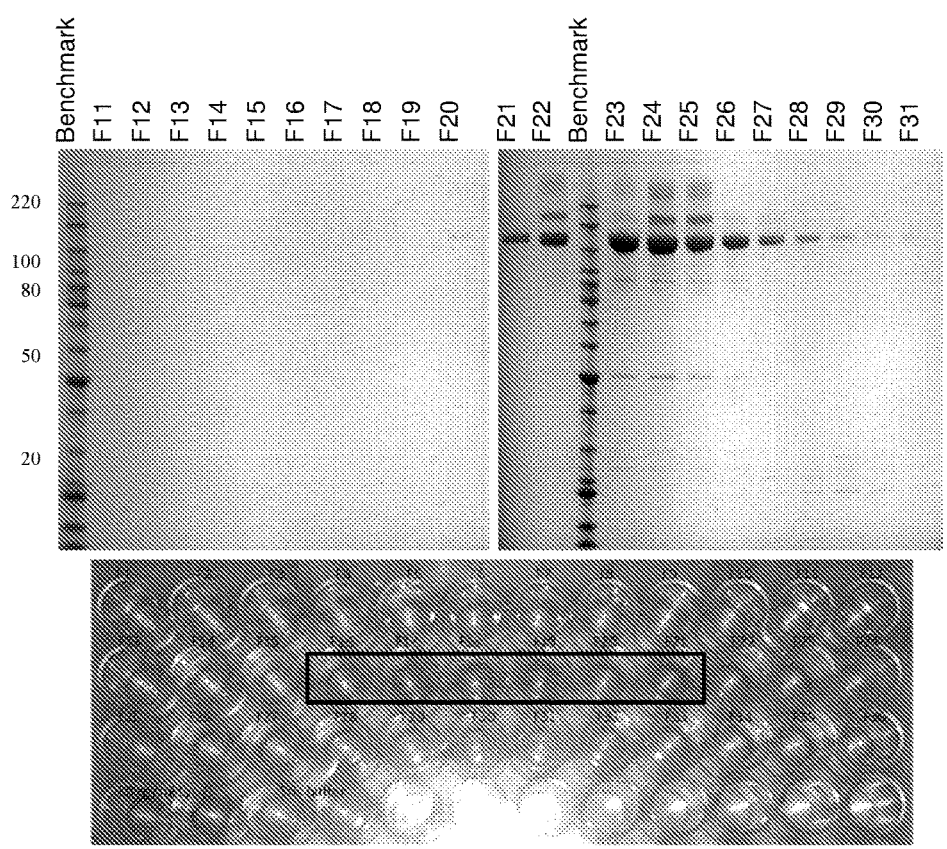

FIG. 11: Removal of Lys-C from rBoNT/A1 by Phenyl HP HIC. Fractions taken from the PhHP HIC polish step, were analysed by SDS-PAGE (top). Recombinant BoNT/A1 has a molecular weight of ~149 kiloDaltons (kDa) and molecular weight markers (Benchmark) are labelled in kDa. Samples of the same fractions were also tested in the colorimetric Lys-C assay (bottom) where the cleavage of substrate releases a yellow chromophore (in the black box).

Figure 12:
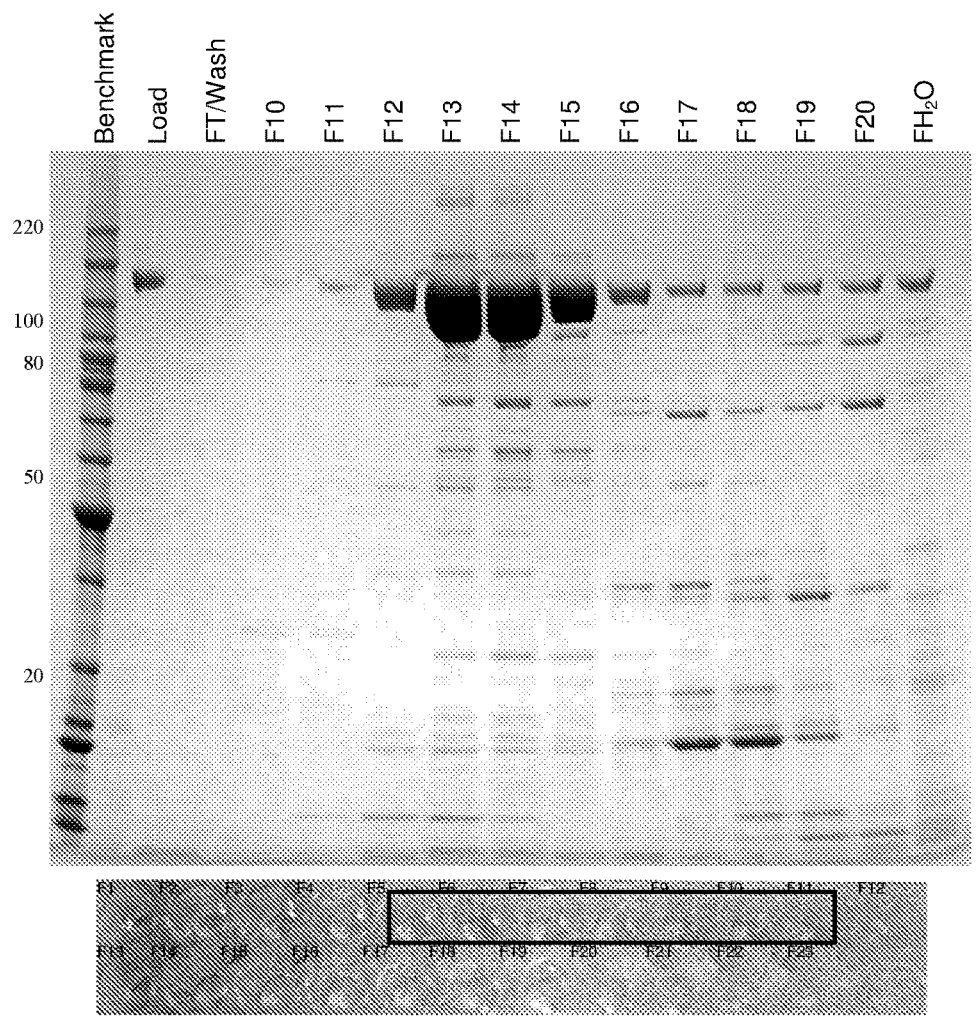

FIG. 12: Removal of Lys-C from rBoNT/A2(0) by Phenyl HP HIC. Fractions taken from the Phenyl HP HIC polish step, were analysed by SDS-PAGE (top). Recombinant BoNT/A1 has a molecular weight of ~149 kDa and molecular weight markers (Benchmark) are labelled in kDa. Samples of the same fractions were also tested in the colorimetric Lys-C assay (bottom) where the cleavage of substrate releases a yellow chromophore (in the black box).

Figure 13:
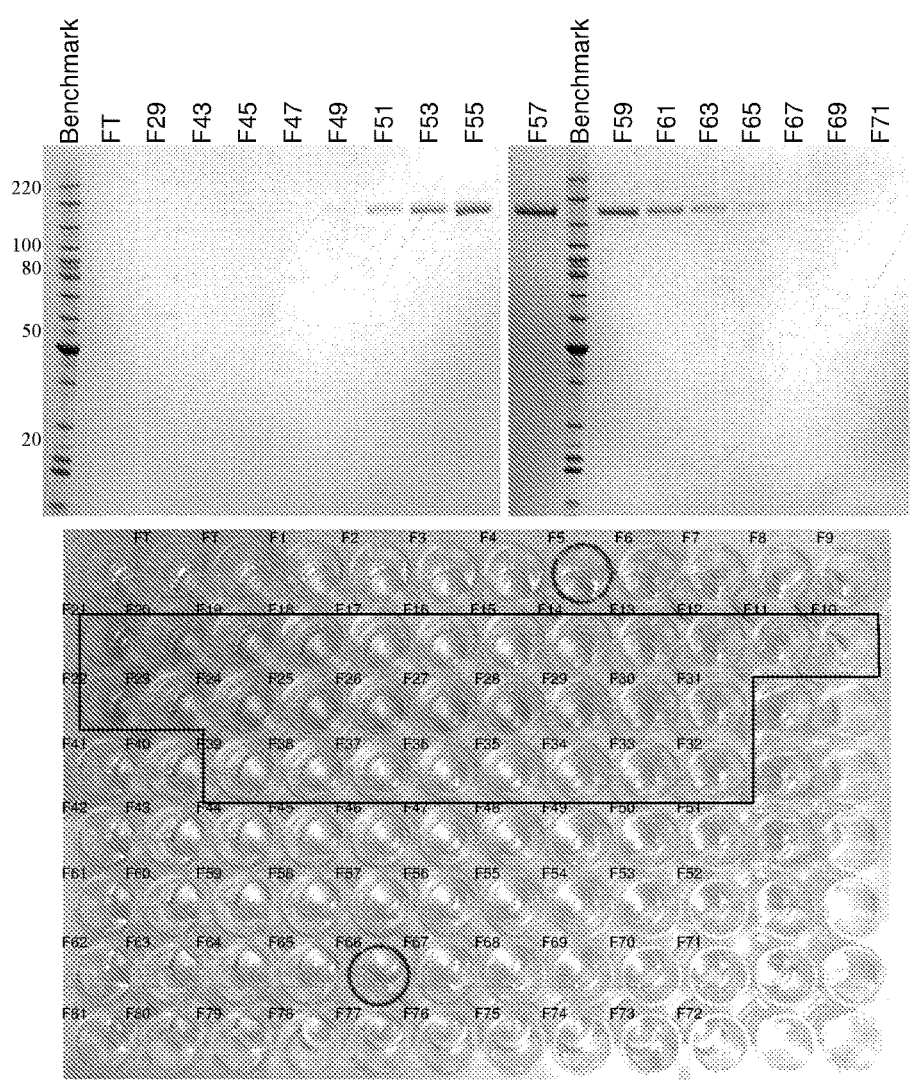

FIG. 13: Removal of Lys-C from rBoNT/A5(0) by Phenyl HP HIC. Fractions taken from the Phenyl HP HIC polish step, were analysed by SDS-PAGE (top). Recombinant BoNT/A5(0) has a molecular weight of ~149 kDa and molecular weight markers (Benchmark) are labelled in kDa. Samples of the same fractions were also tested in the colorimetric Lys-C assay (bottom) where the cleavage of substrate releases a yellow chromophore (in the black box).

Figure 14:
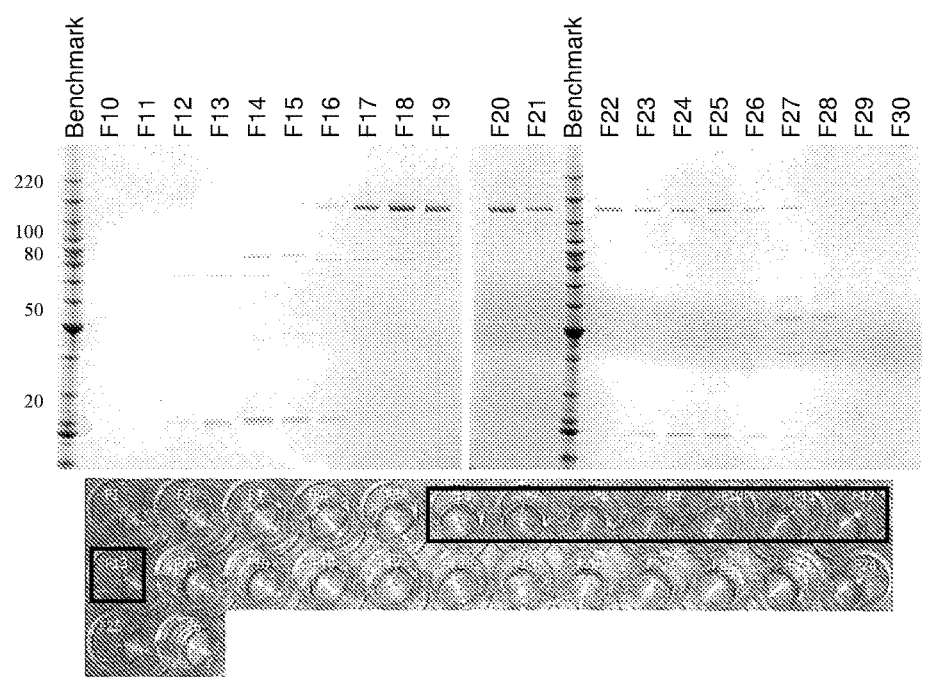

FIG. 14: Removal of Lys-C from rBoNT/A6(0) by Phenyl HP HIC. Fractions taken from the Phenyl HP HIC polish step, were analysed by SDS-PAGE (top). Recombinant BoNT/A6(0) has a molecular weight of ~149 kDa and molecular weight markers (Benchmark) are labelled in kDa. Samples of the same fractions were also tested in the colorimetric Lys-C assay (bottom) where the cleavage of substrate releases a yellow chromophore (in the black box).

Figure 15:
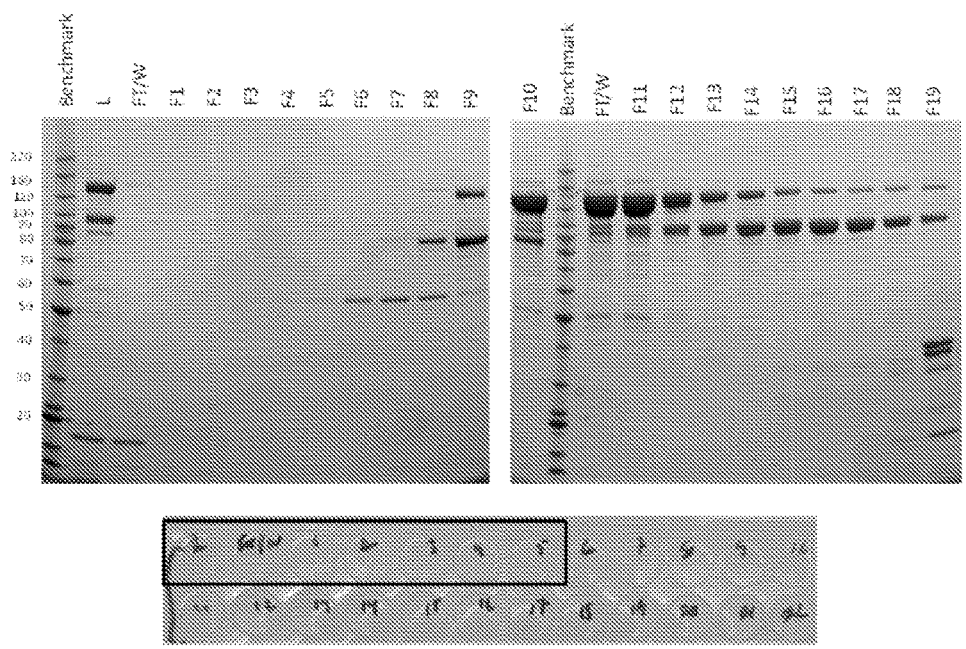

FIG. 15: Removal of Lys-C from mrBoNT/A1 by Butyl HP HIC. Fractions taken from the Butyl HP HIC polish step, were analysed by SDS-PAGE (top). Recombinant mrBoNT/A1 has a molecular weight of ~149 kDa and molecular weight markers (Benchmark) are labelled in kDa. Samples of the same fractions were also tested in the colorimetric Lys-C assay (bottom) where the cleavage of substrate releases a yellow chromophore (in the black box).

EXAMPLES

Example 1

Culturing of Host and Expression of Soluble rBoNT/A Protein

A single colony of BoNT/A transformed in BLR (DE3) cells is used to inoculate a 250 mL conical flask containing 100 mL modified Terrific Broth (mTB) supplemented with 0.2% glucosamine and 30 μg/mL kanamycin. This method would be equally applicable when using a Microbank bead or glycerol stock (10-100 μL) to inoculate the flask.

The flask is incubated for 16 hours at 37° C. with 250 RPM shaking. 10 mL of this starter culture is used to inoculate 2 L conical flasks each containing 1 L supplemented with 0.2% glucosamine and 30 μg/mL kanamycin. Cells are grown at 37° C. for 2 hours at 225 RPM until an $OD_{600}$ of 0.5 is reached. At this point, the culture temperature is dropped to 16° C. After 1 hour, the cells are induced to express BoNT/A by addition of 1 mM IPTG for 20 hours. Cells are harvested by centrifugation for 20 min at 4° C., weighed and then stored at −20° C.

Example 2

Extraction of BoNT/A Protein from Host and Analysis of Expression Level

Expression cell pastes of rBoNT/A are thawed at room temperature and resuspended by pipetting in 3 mL of Tris-NaCl re-suspension buffer per gram of cells supplemented with 10 μL benzonase. Cells are lysed by sonication at 100 W–10×30 s on +45 s off. The lysate is centrifuged at 4000×g for 1 h at 4° C. to obtain the soluble rBoNT/A in the supernatant.

Bradford Assay to Determine Total Protein Concentration of Prepared Lysates

A sample (50 μL) of either diluted rBoNT/A lysate or BSA standard is added to 1 mL disposable cuvettes. 450 μL of Coomassie Bradford Assay reagent is added to each cuvette and allowed to incubate at room temperature for 10 minutes before reading $A_{600}$. The values obtained for the BSA standards are used to determine the amount of protein in the lysate samples.

Semi-Quantitative Western Blot Analysis

A commercial sample of BoNT/A protein purchased from Metabiologics is used to make up SDS-PAGE standards. SDS-PAGE samples of the lysate samples from the expressed cell cultures are then prepared to a known total protein concentration. These samples are loaded onto a polyacrylamide gel and run at 200 V for 50 minutes. Protein bands are electroblotted onto nitrocellulose membrane in methanol free blotting buffer at 0.4 mA for 1 hour. The membranes are blocked for 1 hour with 0.5% BSA in PBS-0.1% Tween 20 and then probed with an antibody to BoNT/A for 1 hour. The blots are further probed with HRP conjugated secondary antibody, developed with SuperSignal DuraWest substrate, and imaged using a Syngene Imaging Instrument.

Example 3

Activation of Botulinum Neurotoxin A (BoNT/A) by Lys-C

Single chain recombinant BoNT/A1 (0.5 mg/mL) dissolved in buffer (50 mM Tris/HCl pH 8.0, 125 mM NaCl) was proteolytically activated by Lys-C(at 1:500 to 1:2500 enzyme:substrate ratio) at 37° C. or 4° C., over a period of 2-20 hr, before the reaction was inhibited with 0.4 μM AEBSF (4-(2-Aminoethyl) benzenesulfonyl fluoride hydrochloride), a specific serine protease inhibitor. This yields the mature di-chain form of BoNT/A1, where the heavy chain is linked to the light chain by a single disulphide bond (data not shown).

The cleavage site was determined to be identical to the endogenous protein by N-terminal sequencing and mass spectrometry, confirming Lys-C to be the activating enzyme of choice (data not shown).

Endoproteinase Lys-C cleavage tests demonstrated that Lys-C cleaved rBoNT/A1 at very low concentrations and remained active over a period of days (data not shown).

Example 4

Purification of Target BoNT/A Protein Free from Activating Protease

Using the BoNT/A primary protein sequence, the properties of BoNT/A and Lys-C were investigated (see Table 2). The predicted properties suggested that both Lys-C and BoNT/A have a similar mean hydropathicity (GRAVY value), but large charge difference at pH 4.5 and 8 (see Table 2).

TABLE 2

Predicted properties of Lys-C and BoNT/A

| Property (calculated) | Lys-C | BoNT/A |
|---|---|---|
| pI | 6.70 | 6.05 |
| % residues charged (DEKR) | 13 | 25 |
| Grand Average of Hydropathicity (GRAVY)* | −0.30 | −0.37 |
| Charge at pH 8.0 | −5 | −12 |
| Charge at pH 4.5 | +13 | +72 |

(*GRAVY = the mean hydropathicity per residue of a molecule (a positive value indicates a hydrophobic molecule))

Based on this information alone, it was predicted that ion exchange (IEX) chromatography would resolve Lys-C from BoNT/A. Therefore, various chromatographic means of purification, including IEX chromatography, were investigated (see below).

Example 5

Screening of Fast Protein Liquid Chromatography (FPLC) Columns for Separating Lys-C from BoNT/A FPLC Purification After BoNT/A1 activation with Lys-C, a number of FPLC columns were tested for polishing and removal of Lys-C:

three hydrophobic interaction chromatography (HIC) columns: Phenyl High Performance (PhHP), Phenyl Fast Flow High substitution (PhFF-Hi), and Butyl HP (BuHP) were tested with Tris pH 8;

three cation exchange chromatography (CEC) columns: Sulphopropyl High Performance (SPHP), Sulphopropyl Fast Flow (SPFF), and Carboxylmethyl Fast Flow (CMFF) were tested with sodium acetate pH 4.5; and four anion exchange chromatography (AEC) columns: Quaternary amine High Performance (QHP), Quaternary amine Fast Flow (QFF), Diethylaminopropyl (DEAP, "ANX"), and Diethylaminoethyl (DEAE)) were tested with Tris pH 8.

Once a sample was loaded onto a column, the column was washed through with buffer to remove any non-specifically bound molecules before applying a linear elution gradient of increasing or decreasing concentration of salt (HIC and CEC/AEC, respectively).

The reaction conditions and purification runs vary between different column types (see Table 3 below).

TABLE 3

Screening conditions for all columns tested for Lys-C resolution

| Column | BoNT/A1 loaded (mg) | Lys-C loaded (µg) | Buffer | Elution gradient |
|---|---|---|---|---|
| PhHP | 1.9 | 1.5 | High-salt, Tris pH 8 | 1-0M, 15 CV |
| BuHP | 1.9 | 1.5 | High-salt, Tris pH 8 | 1-0M, 15 CV |
| PhFF-Hi | 1.5 | 1.2 | High-salt, Tris pH 8 | 1-0M, 15 CV |
| SPHP | 3.4 | 3.0 | Low-salt, NaOAc pH 4.5 | 0-0.5M, 30 CV |
| SPFF | 3.4 | 3.0 | Low-salt, NaOAc pH 4.5 | 0-0.5M, 30 CV |
| CMFF | 3.4 | 3.0 | Low-salt, NaOAc pH 4.5 | 0-0.5M, 30 CV |
| QHP | 2.7 | 2.0 | Low-salt, Tris pH 8 | 0-0.5M, 30 CV |
| QFF | 2.7 | 2.0 | Low-salt, Tris pH 8 | 0-0.5M, 30 CV |
| ANX | 2.7 | 2.0 | Low-salt, Tris pH 8 | 0-0.5M, 30 CV |
| DEAE | 2.7 | 2.0 | Low-salt, Tris pH 8 | 0-0.5M, 30 CV |

FIGS. 1 to 10 show the elution profiles ($A_{280}$) of the BoNT/A1 protein from the various chromatographic columns (dotted lines). The different reaction conditions and purification runs used for the different columns explains the different scales used.

Fractions collected during the elution gradient were analysed with a colorimetric assay to assess Lys-C activity.

Lys-C Activity Colorimetric Assay

This assay involved cleaving a colourless substrate to produce a yellow chromophore that may be detected photometrically by absorption of 405 nm light ($A_{405}$). Thus, this assay provided a simple method to determine if Lys-C was present in each fraction.

Each elution fraction was analysed using said colorimetric Lys-C activity assay and the $A_{405}$ nm measured.

The amount (measured in terms of $A_{405}$) of Lys-C in each of the elution fractions is shown as the bars in FIGS. 1 to 10.

Results

By comparing the $A_{405}$ and $A_{280}$ data (in the graphs of FIGS. 1 to 10), it was possible to deduce which column/s provide the best resolution of Lys-C from BoNT/A.

The different alkyl/aryl groups (Bu and Ph) of the three HIC columns used provide different ligands to which various proteins may interact via the hydrophobic effect. This interaction is further influenced by the density (degree of substitution (Hi/Lo) and bead size (FF/HP)) of these hydrophobic groups. For the CEC columns, the pH of the sample is adjusted to below that of the target protein pI so that it attains an overall net positive charge and is thus able to bind to the column. The different ligands present on each type of column provide different charge densities, and the interaction with different proteins is also influenced by ligand density. These variables similarly apply to the AEC columns where the different chemical groups display different charge densities. In this instance, the pH of the sample is adjusted to above that of the target protein pI so that it attains an overall net negative charge.

The graphical data from FIGS. 1 to 10 is summarised qualitatively in Table 4.

TABLE 4

Summary of qualitative Lys-C/BoNT resolution data

| Chromatography | | Lys-C resolution* |
|---|---|---|
| Hydrophobic interaction[a] | PhHP | ✓✓✓ |
| | BuHP | ✓✓✓ |
| | PhFF-Hi | ✓✓ |

TABLE 4-continued

Summary of qualitative Lys-C/BoNT resolution data

| Chromatography | | | Lys-C resolution* |
|---|---|---|---|
| Ion exchange[b] | Cationic | SPHP | ✓ |
| | | SPFF | ✓ |
| | | CMFF | ✓ |
| | Anionic | QHP | ✓✓ |
| | | QFF | ✓ |
| | | ANX | ✓ |
| | | DEAE | ✓ |

*Apparent resolution of Lys-C with respect to rBoNT/A1. ✓✓✓ = Good, ✓✓ = OK, ✓ = Poor
[a]Phenyl High Performance (PhHP), Phenyl Fast Flow High substitution (PhFF-Hi), Butyl HP (BuHP)
[b]Sulphopropyl High Performance (SPHP), Sulphopropyl Fast Flow (SPFF), Carboxylmethyl Fast Flow (CMFF), Quaternary amine High Performance (QHP), Quaternary amine Fast Flow (QFF), Diethylaminopropyl (DEAP, "ANX"), and Diethylaminoethyl (DEAE)

Percentage Recoveries of Lys-C and Purification after Elution from Each Column Type The total Lys-C signal in each fraction was normalised to the mean $A_{405}$ value from the last 5 fractions of the chromatographic step. From this, the percentage Lys-C present in the protein peak fractions was calculated to indicate the degree of separation of Lys-C from protein based on the elution fractions (Table 5, % LysC in protein peak fractions (normalised)).

With regard to the target protein, it is assumed that all of the BoNT/A molecule elutes under the major peak (i.e., 100% recovery); therefore, the degree of purification may be expressed as the percentage of the total protein loaded which is not recovered in the major peak (Table 5, % Purification).

A good separation of Lys-C from BoNT/A would be one in which we saw a low value for the percentage of LysC in protein peak fractions. From this, it appears that CEC is not able to resolve Lys-C from BoNT/A1. The high performance AEC column, QHP, showed some ability to resolve Lys-C from BoNT/A1. However, it was significantly less effective than the two high performance HIC columns. Therefore, the results demonstrate that, comparing like-for-like (i.e. standard performance vs standard performance and high performance vs high performance), the HIC columns showed improved resolution of Lys-C from BonT/A1 than either the CEC or AEC columns.

The two most promising candidates involve HIC—PhHP and BuHP. Interestingly, these columns both use high performance beads.

The major difference between high performance media and others is that the average particle size is smaller (34 μm vs. 90 μm) and more uniform (24-44 μm vs. 44-165 μm). This is consistent with reported improvements in performance with analytical columns that use smaller sized beads (mean sizes between 3-30 μm) (GE Healthcare handbooks 11-0004-21 & 11-0012-69 and data files 18-1172-87 AE & 18-1172-88 AD).

TABLE 5

Summary of column performance

| Column | % LysC in protein peak fractions (normalised) | % Purification |
|---|---|---|
| PhHP | 5 | 11 |
| BuHP | 7 | 11 |
| PhFF-Hi | 43 | 22 |
| SPHP | 85 | 20 |
| SPFF | 82 | 11 |

TABLE 5-continued

Summary of column performance

| Column | % LysC in protein peak fractions (normalised) | % Purification |
|---|---|---|
| CMFF | 81 | 10 |
| QHP | 26 | 9 |
| QFF | 51 | 6 |
| ANX | 70 | 7 |
| DEAE | 74 | 9 |

PhHP HIC was chosen as the final polish step to resolve away the Lys-C from BoNT/A (see Example 6 below).

Example 6

Activation and Final Purification of Recombinant Botulinum Neurotoxin Sub-Serotype A1 (rBoNT/A1)

Single chain rBoNT/A1 was purified by fast protein liquid chromatography (FPLC) using high-performance butyl sepharose hydrophobic interaction chromatography (Butyl HP HIC) for capture followed by an intermediate purification step with high-performance quaternary ammonium sepharose anionic exchange chromatography (Q HP AEC). This molecule was then incubated with 0.4 μg/mL Lys-C at 37° C. for 2 h to yield the active di-chain.

The Lys-C was resolved from the activated rBoNT/A1 using high-performance phenyl sepharose hydrophobic interaction chromatography (PhHP HIC). This involved adjusting the reaction mixture with a high-salt Tris buffer before loading onto the PhHP column, followed by a high-salt wash and subsequent protein elution with a linear gradient to a low-salt Tris buffer. Elution fractions were analysed by denaturing gel electrophoresis (SDS PAGE—FIG. 11 top) and a colorimetric Lys-C activity assay (FIG. 11 bottom). Lys-C was demonstrated to elute early in the gradient (F16-F21, highlighted in the black box) before the activated BoNT molecule (F21-F29). Thus, this shows good separation of the Lys-C from the rBoNT/A1. The max intensity of the fractions appears to be similar to 30 ng/mL Lys-C, suggesting that any residual Lys-C present in the rBoNT/A1 fractions would be less than this concentration.

Example 7

Activation and Final Purification of Recombinant Endopeptidase-Negative Botulinum Neurotoxin Sub-Serotype A2 (rBoNT/A2(0))

Single chain rBoNT/A2(0) was purified by fast protein liquid chromatography (FPLC) using high-performance butyl sepharose hydrophobic interaction chromatography (Butyl HP HIC) for capture followed by an intermediate purification step with high-performance quaternary ammonium sepharose anionic exchange chromatography (Q HP AEC). This molecule was then incubated with 4 μg/mL Lys-C at 37° C. for 2 h to yield the active di-chain.

The Lys-C was resolved from the activated rBoNT/A2(0) using high-performance phenyl sepharose hydrophobic interaction chromatography (PhHP HIC). This involved adjusting the reaction mixture with a high-salt Tris buffer before loading onto the Phenyl HP column, followed by a high-salt wash and subsequent protein elution with a linear gradient to a low-salt Tris buffer. Elution fractions were analysed by denaturing gel electrophoresis (SDS PAGE) and a colorimetric Lys-C activity assay (FIG. 12)—this showed that the Lys-C eluted early in the gradient (F5-F11) just before the activated BoNT molecule (F12-F15). Thus, this column shows good separation of the Lys-C from the rBoNT/A2(0).

Example 8

Activation and Final Purification of Recombinant Endopeptidase-Negative Botulinum Neurotoxin Sub-Serotype A5 (rBoNT/A5(0))

Single chain rBoNT/A5(0) was purified by fast protein liquid chromatography (FPLC) using high-performance butyl sepharose hydrophobic interaction chromatography (Butyl HP HIC) for capture followed by an intermediate purification step with high-performance quaternary ammonium sepharose anionic exchange chromatography (Q HP AEC). This molecule was then incubated with 2.5 µg/mL Lys-C at 37° C. for 2 h to yield the active di-chain. The Lys-C was resolved from the activated rBoNT/A5(0) using high-performance phenyl sepharose hydrophobic interaction chromatography (Phenyl HP HIC). This involved adjusting the reaction mixture with a high-salt Tris buffer before loading onto the Phenyl HP column, followed by a high-salt wash and subsequent protein elution with a linear gradient to a low-salt Tris buffer. Elution fractions were analysed by denaturing gel electrophoresis (SDS PAGE) and a colorimetric Lys-C activity assay (FIG. 13)—this showed that the Lys-C eluted early in the gradient (F10-F39) before the activated BoNT molecule (F51-F65). Thus, this column shows good separation of the Lys-C from the rBoNT/A5(0).

Example 9

Activation and Final Purification of Recombinant Endopeptidase-Negative Botulinum Neurotoxin Sub-Serotype A6 (rBoNT/A6(0))

Single chain rBoNT/A6(0) was purified first by sodium sulphate precipitation and resolubilisation into sodium acetate before capture with fast protein liquid chromatography (FPLC) using high-performance sulphopropyl sepharose cationic exchange chromatography (SP HP CEC) followed by buffer exchange into Tris buffer at pH 8. This molecule was then incubated with 0.3 µg/mL Lys-C at 37° C. for 2 h to yield the active di-chain. The Lys-C was resolved from the activated rBoNT/A6(0) using high-performance phenyl sepharose hydrophobic interaction chromatography (Phenyl HP HIC). This involved adjusting the reaction mixture with a high-salt Tris buffer before loading onto the Phenyl HP column, followed by a high-salt wash and subsequent protein elution with a linear gradient to a low-salt Tris buffer. Elution fractions were analysed by denaturing gel electrophoresis (SDS PAGE) and a colorimetric Lys-C activity assay (FIG. 14)—this showed that the Lys-C eluted early in the gradient (F6-F13) before the activated BoNT molecule (F16-F27). This shows excellent separation of the Lys-C from the rBoNT/A6(0).

Example 10

Purification of a Single Chain, Recombinant, Cationic, Botulinum Neurotoxin Sub-Serotype A1 Derivative (mrBoNT/A1)

Single chain mrBoNT/A1 (SEQ ID NO: 15) was purified by fast protein liquid chromatography (FPLC) using high-performance sulfopropyl sepharose cation exchange chromatography (SPHP CEX) for capture. An intermediate purification step using high-performance butyl sepharose hydrophobic interaction chromatography (BuHP HIC) was employed to further remove host cell proteins. The BuHP elution fractions were analysed by SDS-PAGE and those containing single chain mrBoNT/A1 pooled as purified, single chain, mrBoNT/A1.

Example 11

Activation and Final Purification of a Recombinant, Cationic, Botulinum Neurotoxin Sub-Serotype A1 Derivative (mrBoNT/A1)

Single chain mrBoNT/A1 (SEQ ID NO: 15) was incubated with 0.4 µg/mL Lys-C at 37° C. for 2 h to yield the active di-chain. The Lys-C was resolved from the activated mrBoNT/A1 using high-performance butyl sepharose hydrophobic interaction chromatography (BuHP HIC). This involved adjusting the reaction mixture with a high-salt Bis-Tris buffer before loading onto the BuHP column, followed by a high-salt wash and subsequent protein elution with a linear gradient to a low-salt Bis-Tris buffer. Elution fractions were analysed by SDS-PAGE (FIG. 15 top) and a colorimetric Lys-C activity assay (FIG. 15 bottom). Lys-C eluted in the column flow through and early in the elution gradient (F1-6, highlighted in the black box, FIG. 15 bottom) before the activated BoNT molecule (F10-F12). Thus, this shows good separation of the Lys-C from the mrBoNT/A1.

Example 12

Formulation Comprising Active Di-Chain BoNT/A Substantially Free from Lys-C

The following six liquid compositions comprising active di-chain BoNT/A are prepared (Table 6).

TABLE 6

| | Exemplary BoNT/A formulations | | | | | |
|---|---|---|---|---|---|---|
| | 1 | 2 | 3 | 4 | 5 | 6 |
| Polysorbate 80 | 0.10 mg/mL | 0.10 mg/mL | 0.10 mg/mL | 0.10 mg/mL | — | — |
| Poloxamer | — | — | — | — | 0.04 mg/mL | 0.04 mg/mL |
| Sucrose | 4.0 mg/mL | — | 4.0 mg/mL | — | 4.0 mg/mL | — |
| Mannitol | — | 4.0 mg/mL | — | 4.0 mg/mL | — | 4.0 mg/mL |
| Sodium Chloride | 8.76 mg/mL | 8.76 mg/mL | 8.76 mg/mL | 8.76 mg/mL | 8.76 mg/mL | 8.76 mg/mL |

TABLE 6-continued

Exemplary BoNT/A formulations

|  | 1 | 2 | 3 | 4 | 5 | 6 |
|---|---|---|---|---|---|---|
| pH | 6.5 | 6.5 | 6.5 | 6.5 | 6.5 | 6.5 |
| Buffer | L-Histidine/ Hydrochloric acid | L-Histidine/ Hydrochloric acid | Di sodium phosphate/ Citric acid anhydrous | Di sodium phosphate/ Citric acid anhydrous | L-Histidine/ Hydrochloric acid | L-Histidine/ Hydrochloric acid |
| Di-Chain BoNT/A | 20 ng/mL | 20 ng/mL | 20 ng/mL | 20 ng/mL | 20 ng/mL | 20 ng/mL |
| MilliQ water | q.s. to 1 mL | q.s. to 1 mL | q.s. to 1 mL | q.s. to 1 mL | q.s. to 1 mL | q.s. to 1 mL |

All six compositions are stored at 25° C. for 12 weeks. The stability of the di-chain BoNT/A protease function is assessed during that period using a cell-free endopeptidase assay.

Example 13

High Se Lys-C Activity Assay

Quantitative determination of final Lys-C concentration in purified BoNT/A samples was done by measuring cleavage of a fluorescent peptide substrate. The fluorescent substrate (Tos-GPK-7-amino-4-trifluoroacetate salt, also called Tos-GPK-AMC) was reconstituted in DMSO to give 20 mg/ml (32.7 mM) stock. This was further diluted to 10 mM with water and aliquots prepared and stored at −20° C. On the day of the assay an appropriate amount of substrate was taken and diluted further with 25 mM Tris pH8, 125 mM NaCl to give a 0.5 mM Lys-C working solution; then Lys-C standards (known concentrations) were prepared by diluting the working solution in assay buffer (25 mM Tris, 125 mM NaCl, 0.1 mg/ml BSA, pH8). Standards, blanks (assay buffer only), and test samples (batches of purified rBoNT/A) were dispensed into black OptiPlate plates, in triplicate (180 μl per well), and equilibrated to 37° C. for 10-15 min. Next, 20 μl of substrate was added and the plate was immediately transferred to a plate reader where a kinetic read was taken. The plate was read using excitation/emission filters—360/40 and 485/20, at 37° C., every 20 min for 5 h. Data were plotted as time in minutes (x axis) against absorbance/fluorescence (y axis). Slope values for each Lys-C concentration were used to generate a standard curve for Lys-C concentration. Samples of purified rBoNT/A were treated in the same way and the Lys-C concentration in each rBoNT/A sample was interpolated from the standard curve. Based on analysis of four independent batches or rBoNT/A we measured average Lys-C concentration in the final material to be 7.3±1.5 pg Lys-C per 100 ng/BoNT/A.

The invention claimed is:

1. A method for producing soluble di-chain BoNT/A protein, said method comprising:
   a) providing a soluble single-chain BoNT/A protein;
   b) contacting said BoNT/A protein with endoproteinase Lys-C (Lys-C) in solution; and
   c) separating the soluble BoNT/A protein from the Lys-C by contacting the solution containing soluble BoNT/A protein and Lys-C with a hydrophobic surface, wherein the soluble BoNT/A protein binds with preference to the hydrophobic surface.

2. The method according to claim 1, wherein the soluble single-chain BoNT/A protein is produced (i) in a host cell, by expressing a nucleic acid encoding said single-chain BoNT/A protein in an expression system; or (ii) in an in vitro expression system.

3. The method according to claim 2, wherein the host cell is a bacterial host cell and the expression system is a bacterial expression system.

4. The method according to claim 3, wherein the bacterial expression system is an *E. coli* expression system and the host cell is an *E. coli* cell.

5. The method according to claim 2, wherein said soluble single-chain BoNT/A protein is expressed in the cytoplasm of said host cell.

6. The method according to claim 2, wherein said soluble single-chain BoNT/A protein is expressed at a level of at least 5 mg/L.

7. The method according to claim 2, comprising lysis of the bacterial or *E. coli* host cell to provide a bacterial or *E. coli* host cell homogenate containing said soluble single-chain BoNT/A protein.

8. The method according to claim 1, wherein the hydrophobic surface is an inert matrix to which a ligand consisting of aryl or alkyl groups is attached.

9. The method according to claim 8, wherein the ligand is selected from the group consisting of: butyl, phenyl and octyl ligands.

10. The method according to claim 9, wherein a high performance hydrophobic surface is used.

* * * * *

SEQUENCE LISTING

```
<160> NUMBER OF SEQ ID NOS: 15

<210> SEQ ID NO 1
<211> LENGTH: 1296
<212> TYPE: PRT
<213> ORGANISM: Clostridium Botulinum

<400> SEQUENCE: 1

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140
```

```
Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
    435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560
```

-continued

His Gly Lys Ser Arg Ile Ala Leu Thr Asn Ser Val Asn Glu Ala Leu
            565                 570                 575

Leu Asn Pro Ser Arg Val Tyr Thr Phe Phe Ser Ser Asp Tyr Val Lys
        580                 585                 590

Lys Val Asn Lys Ala Thr Glu Ala Ala Met Phe Leu Gly Trp Val Glu
            595                 600                 605

Gln Leu Val Tyr Asp Phe Thr Asp Glu Thr Ser Glu Val Ser Thr Thr
        610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
        690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
            725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
        820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
            885                 890                 895

Lys Ile Asn Ile Gly Ser Lys Val Asn Phe Asp Pro Ile Asp Lys Asn
        900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
            965                 970                 975

Ser Leu Asn Tyr Gly Glu Ile Ile Trp Thr Leu Gln Asp Thr Gln Glu

```
              980             985             990
Ile Lys Gln Arg Val Val Phe Lys Tyr Ser Gln Met Ile Asn Ile Ser
        995            1000            1005

Asp Tyr Ile Asn Arg Trp Ile Phe Val Thr Ile Thr Asn Asn Arg
    1010            1015            1020

Leu Asn Asn Ser Lys Ile Tyr Ile Asn Gly Arg Leu Ile Asp Gln
    1025            1030            1035

Lys Pro Ile Ser Asn Leu Gly Asn Ile His Ala Ser Asn Asn Ile
    1040            1045            1050

Met Phe Lys Leu Asp Gly Cys Arg Asp Thr His Arg Tyr Ile Trp
    1055            1060            1065

Ile Lys Tyr Phe Asn Leu Phe Asp Lys Glu Leu Asn Glu Lys Glu
    1070            1075            1080

Ile Lys Asp Leu Tyr Asp Asn Gln Ser Asn Ser Gly Ile Leu Lys
    1085            1090            1095

Asp Phe Trp Gly Asp Tyr Leu Gln Tyr Asp Lys Pro Tyr Tyr Met
    1100            1105            1110

Leu Asn Leu Tyr Asp Pro Asn Lys Tyr Val Asp Val Asn Asn Val
    1115            1120            1125

Gly Ile Arg Gly Tyr Met Tyr Leu Lys Gly Pro Arg Gly Ser Val
    1130            1135            1140

Met Thr Thr Asn Ile Tyr Leu Asn Ser Ser Leu Tyr Arg Gly Thr
    1145            1150            1155

Lys Phe Ile Ile Lys Lys Tyr Ala Ser Gly Asn Lys Asp Asn Ile
    1160            1165            1170

Val Arg Asn Asn Asp Arg Val Tyr Ile Asn Val Val Val Lys Asn
    1175            1180            1185

Lys Glu Tyr Arg Leu Ala Thr Asn Ala Ser Gln Ala Gly Val Glu
    1190            1195            1200

Lys Ile Leu Ser Ala Leu Glu Ile Pro Asp Val Gly Asn Leu Ser
    1205            1210            1215

Gln Val Val Val Met Lys Ser Lys Asn Asp Gln Gly Ile Thr Asn
    1220            1225            1230

Lys Cys Lys Met Asn Leu Gln Asp Asn Asn Gly Asn Asp Ile Gly
    1235            1240            1245

Phe Ile Gly Phe His Gln Phe Asn Asn Ile Ala Lys Leu Val Ala
    1250            1255            1260

Ser Asn Trp Tyr Asn Arg Gln Ile Glu Arg Ser Ser Arg Thr Leu
    1265            1270            1275

Gly Cys Ser Trp Glu Phe Ile Pro Val Asp Asp Gly Trp Gly Glu
    1280            1285            1290

Arg Pro Leu
    1295

<210> SEQ ID NO 2
<211> LENGTH: 25
<212> TYPE: PRT
<213> ORGANISM: Clostridium Botulinum

<400> SEQUENCE: 2

Cys Val Arg Gly Ile Ile Thr Ser Lys Thr Lys Ser Leu Asp Lys Gly
1               5                   10                  15

Tyr Asn Lys Ala Leu Asn Asp Leu Cys
            20                  25
```

```
<210> SEQ ID NO 3
<211> LENGTH: 25
<212> TYPE: PRT
<213> ORGANISM: Clostridium Botulinum

<400> SEQUENCE: 3

Cys Val Arg Gly Ile Ile Pro Phe Lys Thr Lys Ser Leu Asp Glu Gly
1               5                   10                  15

Tyr Asn Lys Ala Leu Asn Asp Leu Cys
            20                  25

<210> SEQ ID NO 4
<211> LENGTH: 25
<212> TYPE: PRT
<213> ORGANISM: Clostridium Botulinum

<400> SEQUENCE: 4

Cys Val Arg Gly Ile Ile Pro Phe Lys Thr Lys Ser Leu Asp Glu Gly
1               5                   10                  15

Tyr Asn Lys Ala Leu Asn Asp Leu Cys
            20                  25

<210> SEQ ID NO 5
<211> LENGTH: 25
<212> TYPE: PRT
<213> ORGANISM: Clostridium Botulinum

<400> SEQUENCE: 5

Cys Val Arg Gly Ile Ile Pro Phe Lys Thr Lys Ser Leu Asp Glu Gly
1               5                   10                  15

Tyr Asn Lys Ala Leu Asn Tyr Leu Cys
            20                  25

<210> SEQ ID NO 6
<211> LENGTH: 25
<212> TYPE: PRT
<213> ORGANISM: Clostridium Botulinum

<400> SEQUENCE: 6

Cys Val Arg Gly Ile Ile Thr Ser Lys Thr Lys Ser Leu Asp Glu Gly
1               5                   10                  15

Tyr Asn Lys Ala Leu Asn Glu Leu Cys
            20                  25

<210> SEQ ID NO 7
<211> LENGTH: 25
<212> TYPE: PRT
<213> ORGANISM: Clostridium Botulinum

<400> SEQUENCE: 7

Cys Val Arg Gly Ile Ile Thr Ser Lys Thr Lys Ser Leu Asp Glu Gly
1               5                   10                  15

Tyr Asn Lys Ala Leu Asn Asp Leu Cys
            20                  25

<210> SEQ ID NO 8
<211> LENGTH: 333
<212> TYPE: PRT
<213> ORGANISM: Clostridium Botulinum

<400> SEQUENCE: 8

Val Gln Gly Gln Ser Val Lys Gly Val Gly Lys Thr Ser Leu Asp Gly
```

```
            1               5                  10                 15
          Leu Val Asn Ile Asp Val Thr Tyr Gly Asn Gly Lys Tyr Tyr Leu Lys
                        20                 25                 30

Asp Ser Asn Lys Asn Ile Tyr Leu Tyr Asp Leu Lys Asn Gln Val Asp
                        35                 40                 45

Glu Tyr Asp Leu Tyr Asn Tyr Leu Ser Arg Pro Asn Tyr Lys Gln Ile
                        50                 55                 60

Leu Met Ser Lys Ser Glu Leu Ile Ser Asn Tyr Asn Asn Asn Phe Ile
           65                70                 75                 80

Ala Asn Asn Gln Val Asn Ser Val Asp Ala Tyr Val Asn Thr Asn Lys
                        85                 90                 95

Thr Tyr Asp Tyr Tyr Lys Asn Lys Leu Asn Arg Asn Ser Ile Asp Asn
                       100                105                110

Lys Gly Met Asn Ile Asn Gly Phe Val His Val Gly Arg Asn Tyr Gly
                       115                120                125

Asn Ala Phe Trp Tyr Gly Pro Tyr Asp Gly Met Phe Phe Gly Asp Gly
                       130                135                140

Asp Gly Ile Tyr Phe Ser Ser Leu Ala Lys Ser Leu Asp Val Val Gly
          145                150                155                160

His Glu Leu Ser His Gly Val Thr Asn Lys Glu Ser Asn Leu Lys Tyr
                       165                170                175

Glu Asn Glu Ser Gly Ala Leu Asn Glu Ser Phe Ser Asp Ile Met Gly
                       180                185                190

Val Ala Val Glu Gly Lys Asn Phe Val Leu Gly Glu Asp Cys Trp Val
                       195                200                205

Ala Gly Gly Val Met Arg Asp Met Glu Asn Pro Ser Arg Gly Gly Gln
                       210                215                220

Pro Ala His Met Lys Asp Tyr Lys Tyr Lys Thr Met Asn Asp Asp Asn
          225                230                235                240

Gly Gly Val His Thr Asn Ser Gly Ile Ile Asn His Ala Ala Tyr Leu
                       245                250                255

Val Ala Asp Gly Ile Glu Lys Thr Gly Ala Lys Asn Ser Lys Asp Ile
                       260                265                270

Met Gly Lys Ile Phe Tyr Thr Ala Asn Cys Tyr Lys Trp Asp Glu Thr
                       275                280                285

Thr Asn Phe Ala Lys Cys Arg Asn Asp Val Val Gln Val Thr Lys Glu
                       290                295                300

Leu Tyr Gly Glu Asn Ser Asn Tyr Val Lys Ile Val Glu Lys Ala Phe
          305                310                315                320

Asp Gln Val Gly Ile Thr Ala Thr Pro Gln Leu Pro Leu
                       325                330

<210> SEQ ID NO 9
          <211> LENGTH: 581
          <212> TYPE: PRT
          <213> ORGANISM: Clostridium Botulinum

<400> SEQUENCE: 9

Met Lys Ser Lys Lys Leu Leu Ala Thr Val Leu Ser Ala Val Ile Thr
           1               5                  10                 15

Phe Ser Thr Val Ser Ala Val Tyr Ala Ala Pro Val Gly Lys Glu Ser
                        20                 25                 30

Lys Val Glu Pro Lys Thr Thr Thr Ile Thr Trp Glu Lys Asn Glu Gln
                        35                 40                 45
```

```
Asn Thr Lys Lys Ala Ala Thr Asp Ile Thr Glu Lys Lys Phe Asn Asn
 50                  55                  60

Ser Glu Glu Ile Thr Lys Phe Phe Glu Lys Asn Ile Ser Lys Phe Gly
 65                  70                  75                  80

Val Gln Lys Gly Ser Leu Lys Asn Thr Lys Thr Val Lys Asp Glu Lys
                 85                  90                  95

Gly Lys Thr Asn Tyr His Met Ile Tyr Glu Val Glu Gly Ile Pro Val
            100                 105                 110

Tyr Tyr Gly Arg Ile Val Phe Thr Thr Glu Lys Asp Ser Ser Met Asp
            115                 120                 125

Ser Ile Asn Gly Arg Ile Asp Thr Val Phe Glu Asn Gly Asn Trp Lys
 130                 135                 140

Asn Lys Ile Lys Leu Ser Lys Glu Asp Ala Ile Ala Lys Ala Lys Asn
145                 150                 155                 160

Asp Ile Lys Asp Glu Lys Ala Thr Ser Lys Lys Thr Asp Leu Tyr Leu
                165                 170                 175

Tyr Asn Phe Glu Gly Lys Pro Tyr Val Val Tyr Leu Val Asp Leu Ile
            180                 185                 190

Thr Asp Asn Gly Ser Trp Thr Val Phe Val Asn Ala Glu Asp Gly Ser
            195                 200                 205

Ile Val Asn Lys Phe Asn Asn Thr Pro Thr Leu Ile Asp Thr Lys Asp
 210                 215                 220

Gln Lys Leu Pro Asn Ala Lys Lys Ile Lys Asp Glu Ala Lys Lys Ala
225                 230                 235                 240

Ser Asn Ala Asn Asn Val Ile Asp Val Gln Gly Gln Ser Val Lys Gly
                245                 250                 255

Val Gly Lys Thr Ser Leu Asp Gly Leu Val Asn Ile Asp Val Thr Tyr
            260                 265                 270

Gly Asn Gly Lys Tyr Tyr Leu Lys Asp Ser Asn Lys Asn Ile Tyr Leu
            275                 280                 285

Tyr Asp Leu Lys Asn Gln Val Asp Glu Tyr Asp Leu Tyr Asn Tyr Leu
            290                 295                 300

Ser Arg Pro Asn Tyr Lys Gln Ile Leu Met Ser Lys Ser Glu Leu Ile
305                 310                 315                 320

Ser Asn Tyr Asn Asn Phe Ile Ala Asn Asn Gln Val Asn Ser Val
                325                 330                 335

Asp Ala Tyr Val Asn Thr Asn Lys Thr Tyr Asp Tyr Lys Asn Lys
            340                 345                 350

Leu Asn Arg Asn Ser Ile Asp Asn Lys Gly Met Asn Ile Asn Gly Phe
            355                 360                 365

Val His Val Gly Arg Asn Tyr Gly Asn Ala Phe Trp Tyr Gly Pro Tyr
    370                 375                 380

Asp Gly Met Phe Phe Gly Asp Gly Asp Gly Ile Tyr Phe Ser Ser Leu
385                 390                 395                 400

Ala Lys Ser Leu Asp Val Val Gly His Glu Leu Ser His Gly Val Thr
                405                 410                 415

Asn Lys Glu Ser Asn Leu Lys Tyr Glu Asn Glu Ser Gly Ala Leu Asn
            420                 425                 430

Glu Ser Phe Ser Asp Ile Met Gly Val Ala Val Glu Gly Lys Asn Phe
            435                 440                 445

Val Leu Gly Glu Asp Cys Trp Val Ala Gly Gly Val Met Arg Asp Met
450                 455                 460

Glu Asn Pro Ser Arg Gly Gly Gln Pro Ala His Met Lys Asp Tyr Lys
```

```
                                     465                 470                 475                 480
Tyr Lys Thr Met Asn Asp Asn Gly Gly Val His Thr Asn Ser Gly
                485                 490                 495
Ile Ile Asn His Ala Ala Tyr Leu Val Ala Asp Gly Ile Glu Lys Thr
                500                 505                 510
Gly Ala Lys Asn Ser Lys Asp Ile Met Gly Lys Ile Phe Tyr Thr Ala
                515                 520                 525
Asn Cys Tyr Lys Trp Asp Glu Thr Thr Asn Phe Ala Lys Cys Arg Asn
        530                 535                 540
Asp Val Val Gln Val Thr Lys Glu Leu Tyr Gly Glu Asn Ser Asn Tyr
545                 550                 555                 560
Val Lys Ile Val Glu Lys Ala Phe Asp Gln Val Gly Ile Thr Ala Thr
                565                 570                 575
Pro Gln Leu Pro Leu
            580
```

<210> SEQ ID NO 10
<211> LENGTH: 1005
<212> TYPE: DNA
<213> ORGANISM: Clostridium Botulinum

<400> SEQUENCE: 10

```
atggttcaag gtcaaagcgt taaaggagta ggaaaaacta gcttggatgg actagtaaat      60
attgatgtaa cttatggaaa tggaaaatac tatttaaaag atagcaacaa aaatatttat     120
ctatatgact aaaaaatca agttgatgaa tatgatctat acaattatct tagtagacct      180
aactataaac aaatattaat gagcaaatct gaattaatat ctaattacaa taataatttt     240
atagccaaca atcaggttaa ttctgtagat gcttatgtaa acacaaataa aacctatgat     300
tattataaaa acaaattaaa tagaaacagt attgataata agggtatgaa tattaatggg     360
tttgttcatg taggtagaaa ttatggtaat gcttttttggt acgtccata tgatgggatg     420
ttctttggcg atggcgacgg aatatacttc tcttcccttg caaaatcttt agatgttgta     480
ggccacgaat taagtcatgg tgtaacaaat aaagagtcta atcttaaata tgaaaatgaa     540
tctggtgccc taaatgaatc tttctcagat attatgggag tagctgttga gggtaaaaac     600
tttgtactag gtgaagattg ctgggttgct ggaggagtaa tgagagatat ggaaaatcca     660
tccagaggag gccaaccagc tcatatgaaa gattataaat acaaaactat gaatgacgat     720
aacggtggtg ttcatacaaa ttcaggtata ataaaccatg ctgcttattt agttgcagat     780
ggaatagaaa aaactggtgc aaaaaatagt aaagatatta tgggaaaaat attctataca     840
gctaattgct ataatgggga tgaaacaaca aatttttgcta agtgcagaaa tgatgtagtc     900
caagttacta agaacttta tggcgaaaat agcaactatg taaaaattgt tgaaaaagct     960
tttgaccaag ttggaataac tgctacacct caattaccat ataa               1005
```

<210> SEQ ID NO 11
<211> LENGTH: 1746
<212> TYPE: DNA
<213> ORGANISM: Clostridium Botulinum

<400> SEQUENCE: 11

```
atgaaaagta aaaattatt agctacagtg ctaagtgccg tgatcacttt ttctactgtt       60
tctgcagttt atgctgcgcc tgtaggaaaa gaaagtaaag ttgaaccaaa aactacaaca     120
ataacttggg aaaaaaatga acaaaatact aaaaaagctg ctactgatat aactgaaaag     180
```

```
aaatttaaca attctgagga gataactaaa ttctttgaaa aaatatatc taaatttggt      240
gtacaaaaag ttctcttaa aaacaccaag actgtaaaag acgaaaaagg taaaactaac      300
tatcatatga tttatgaagt agaaggtata cctgtatact atggaagaat tgtttttaca     360
actgaaaaag actcctccat ggattctata acggtagaa ttgatactgt ttttgaaaat      420
gggaattgga aaacaaaat caaactatca aagaagatg ctatagcaaa agctaaaaat      480
gatattaaag atgaaaaagc aactagtaaa aagaccgatt tatatctgta aattttgag     540
ggcaaacctt atgtagttta tttagtagat ctaattacag acaacgggag ttggacggtt    600
ttcgttaatg ctgaggatgg ttctatagta aataaattta ataatactcc tactttaatt   660
gatactaaag atcaaaaatt acccaatgct aaaaaaatta agatgaagc taaaaaagct     720
agtaatgcaa ataatgtaat tgatgttcaa ggtcaaagcg ttaaaggagt aggaaaaact    780
agcttggatg gactagtaaa tattgatgta acttatggaa atggaaaata ctatttaaaa    840
gatagcaaca aaatattta tctatatgac ttaaaaaatc aagttgatga atatgatcta     900
tacaattatc ttagtagacc taactataaa caaatattaa tgagcaaatc tgaattaata   960
tctaattaca ataataattt tatagccaac aatcaggtta attctgtaga tgcttatgta  1020
aacacaaata aaacctatga ttattataaa acaaattaa atagaaacag tattgataat   1080
aagggtatga atattaatgg gtttgttcat gtaggtagaa attatggtaa tgcttttttgg 1140
tacggtccat atgatgggat gttctttggc gatggcgacg gaatatactt ctcttccctt  1200
gcaaaatctt tagatgttgt aggccacgaa ttaagtcatg gtgtaacaaa taaagagtct  1260
aatcttaaat atgaaaatga atctggtgcc taaatgaat cttctctcaga tattatggga  1320
gtagctgttg agggtaaaaa ctttgtacta ggtgaagatt gctgggttgc tggaggagta  1380
atgagagata tggaaaatcc atccagagga ggccaaccag ctcatatgaa agattataaa  1440
tacaaaacta tgaatgacga taacggtggt gttcatacaa attcaggtat aataaaccat  1500
gctgcttatt tagttgcaga tggaatagaa aaaactggtg caaaaaatag taaagatatt  1560
atgggaaaaa tattctatac agctaattgc tataaatggg atgaaacaac aaattttgct  1620
aagtgcagaa atgatgtagt ccaagttact aaagaacttt atggcgaaaa tagcaactat  1680
gtaaaaattg ttgaaaaagc ttttgaccaa gttggaataa ctgctacacc tcaattacca  1740
ttataa                                                              1746
```

```
<210> SEQ ID NO 12
<211> LENGTH: 16
<212> TYPE: PRT
<213> ORGANISM: Artificial Sequence
<220> FEATURE:
<223> OTHER INFORMATION: Strep tag

<400> SEQUENCE: 12

Val Pro Pro Thr Pro Gly Ser Ala Trp Ser His Pro Gln Phe Glu Lys
1               5                   10                  15

<210> SEQ ID NO 13
<211> LENGTH: 25
<212> TYPE: PRT
<213> ORGANISM: Clostridium botulinum

<400> SEQUENCE: 13

Cys Val Arg Gly Ile Ile Thr Ser Lys Thr Lys Ser Leu Asp Glu Gly
1               5                   10                  15

Tyr Asn Lys Ala Leu Asn Asp Leu Cys
```

```
                         20                  25

<210> SEQ ID NO 14
<211> LENGTH: 25
<212> TYPE: PRT
<213> ORGANISM: Clostridium botulinum

<400> SEQUENCE: 14

Cys Val Arg Gly Ile Ile Pro Phe Lys Thr Lys Ser Leu Asp Glu Gly
1               5                   10                  15

Tyr Asn Lys Ala Leu Asn Asp Leu Cys
            20                  25

<210> SEQ ID NO 15
<211> LENGTH: 1296
<212> TYPE: PRT
<213> ORGANISM: Clostridium botulinum

<400> SEQUENCE: 15

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
```

```
            290                 295                 300
Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
        450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
                500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
        530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Met Phe Leu Gly Trp Val Glu
            595                 600                 605

Gln Leu Val Tyr Asp Phe Thr Asp Glu Thr Ser Glu Val Ser Thr Thr
        610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
        690                 695                 700

Lys Trp Asp Glu Val Tyr Lys Tyr Ile Val Thr Asn Trp Leu Ala Lys
705                 710                 715                 720
```

```
Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Lys His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Lys Ala Ile Val Tyr Asn Ser Met Tyr Glu Asn Phe Ser Thr Ser
    930                 935                 940

Phe Trp Ile Arg Ile Pro Lys Tyr Phe Asn Lys Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Lys Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg
    1010                1015                1020

Leu Asn Lys Ser Lys Ile Tyr Ile Asn Gly Arg Leu Ile Asp Gln
    1025                1030                1035

Lys Pro Ile Ser Asn Leu Gly Asn Ile His Ala Ser Asn Lys Ile
    1040                1045                1050

Met Phe Lys Leu Asp Gly Cys Arg Asp Thr His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asp Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125
```

-continued

```
Gly Ile Arg Gly Tyr Met Tyr Leu Lys Gly Pro Arg Gly Ser Val
    1130                1135                1140

Met Thr Thr Asn Ile Tyr Leu Asn Ser Ser Leu Tyr Arg Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
    1190                1195                1200

Lys Ile Leu Ser Ala Leu Glu Ile Pro Asp Val Gly Asn Leu Ser
    1205                1210                1215

Gln Val Val Val Met Lys Ser Lys Asn Asp Lys Gly Ile Thr Asn
    1220                1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Ser Arg Thr Leu
    1265                1270                1275

Gly Cys Ser Trp Glu Phe Ile Pro Val Asp Asp Gly Trp Gly Glu
    1280                1285                1290

Arg Pro Leu
    1295
```